United States Patent
Lamson et al.

(10) Patent No.: US 12,121,228 B2
(45) Date of Patent: Oct. 22, 2024

(54) EXPANDABLE TISSUE ENGAGEMENT APPARATUS AND METHOD

(71) Applicant: Teleflex Life Sciences LLC, Wilmington, DE (US)

(72) Inventors: Theodore C. Lamson, Pleasanton, CA (US); Theodore Bender, San Anselmo, CA (US); Jolene Cutts, San Francisco, CA (US); Robert M. George, San Jose, CA (US); Jennifer Kiyoi, Pleasanton, CA (US); Daniel Merrick, Dublin, CA (US); Ailee Pham, Milpitas, CA (US); Maheshwara Rao, Oakland, CA (US); Christopher Zaler, Los Gatos, CA (US); Curtis Yarra, Oakland, CA (US); Kevin Alexander Lessard, San Francisco, CA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 0 days.

(21) Appl. No.: 18/188,942

(22) Filed: Mar. 23, 2023

(65) Prior Publication Data
US 2023/0225720 A1    Jul. 20, 2023

Related U.S. Application Data

(63) Continuation of application No. 16/577,013, filed on Sep. 20, 2019, now Pat. No. 11,672,520, which is a
(Continued)

(51) Int. Cl.
*A61B 17/02* (2006.01)
*A61B 17/00* (2006.01)
(Continued)

(52) U.S. Cl.
CPC ...... *A61B 17/0218* (2013.01); *A61B 17/3478* (2013.01); *A61M 29/00* (2013.01);
(Continued)

(58) Field of Classification Search
CPC ... A61B 17/0218; A61B 17/08; A61B 17/083; A61B 17/10; A61B 17/122;
(Continued)

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| CA | 2477220 | 11/2007 |
| CN | 1697633 A | 11/2005 |

(Continued)

OTHER PUBLICATIONS

European Extended Search Report and Search Opinion mailed Jun. 16, 2023, in EP Application No. 23169061.1.
(Continued)

*Primary Examiner* — Kankindi Rwego
(74) *Attorney, Agent, or Firm* — Dorsey & Whitney LLP

(57) ABSTRACT

A system and associated method for manipulating tissues and anatomical or other structures in medical applications for the purpose of treating diseases or disorders or other purposes. In one aspect, the system includes an expandable structure for enhancing engagement with median lobe prostate tissue.

8 Claims, 22 Drawing Sheets

Related U.S. Application Data continuation of application No. PCT/US2018/067229, filed on Dec. 21, 2018.

(60) Provisional application No. 62/610,184, filed on Dec. 23, 2017.

(51) Int. Cl.
| | | |
|---|---|---|
| *A61B 17/04* | (2006.01) | |
| *A61B 17/22* | (2006.01) | |
| *A61B 17/34* | (2006.01) | |
| *A61M 29/00* | (2006.01) | |
| *A61B 90/00* | (2016.01) | |

(52) U.S. Cl.
CPC ............ *A61B 2017/00274* (2013.01); *A61B 2017/00858* (2013.01); *A61B 2017/00951* (2013.01); *A61B 2017/0409* (2013.01); *A61B 2017/22072* (2013.01); *A61B 2090/0811* (2016.02); *A61M 2210/166* (2013.01)

(58) Field of Classification Search
CPC ............ A61B 17/1227; A61B 17/128; A61B 17/1285; A61B 17/3478; A61B 2017/00274; A61B 2017/00951; A61B 2017/0409; A61B 2017/0417; A61B 2017/0419; A61B 2017/22072; A61B 2017/081; A61B 2017/00858; A61B 2090/0811; A61M 29/00; A61M 2210/166; A61F 2/2463; A61F 2/2466
USPC .......................................................... 600/37
See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,452,236 A | 6/1984 | Utsugi |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson et al. |
| 4,926,860 A | 5/1990 | Stice et al. |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gatturna |
| 4,994,066 A | 2/1991 | Voss |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gatturna et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,163,960 A | 11/1992 | Bonutti |
| 5,167,614 A | 12/1992 | Tessmann et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,254,126 A | 10/1993 | Filipi et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,350,399 A | 9/1994 | Erlebacher et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,370,661 A | 12/1994 | Branch |
| 5,372,600 A | 12/1994 | Beyar et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash et al. |
| 5,417,691 A | 5/1995 | Hayhurst |
| 5,435,805 A | 7/1995 | Edwards et al. |
| 5,441,485 A | 8/1995 | Peters |
| 5,458,612 A | 10/1995 | Chin |
| 5,464,416 A | 11/1995 | Steckel |
| 5,470,308 A | 11/1995 | Edwards et al. |
| 5,470,337 A | 11/1995 | Moss |
| 5,472,446 A | 12/1995 | Torre |
| 5,480,406 A | 1/1996 | Nolan et al. |
| 5,499,994 A | 3/1996 | Tihon et al. |
| 5,501,690 A | 3/1996 | Measamer et al. |

(56) References Cited

U.S. PATENT DOCUMENTS

| | | |
|---|---|---|
| 5,507,754 A | 4/1996 | Green et al. |
| 5,522,846 A | 6/1996 | Bonutti |
| 5,531,759 A | 7/1996 | Kensey et al. |
| 5,531,763 A | 7/1996 | Mastri et al. |
| 5,534,012 A | 7/1996 | Bonutti |
| 5,536,240 A | 7/1996 | Edwards et al. |
| 5,540,655 A | 7/1996 | Edwards et al. |
| 5,540,701 A | 7/1996 | Sharkey et al. |
| 5,540,704 A | 7/1996 | Gordon et al. |
| 5,542,594 A | 8/1996 | McKean et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,688 A | 10/1996 | Riza |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,591,179 A | 1/1997 | Edelstein |
| 5,593,421 A | 1/1997 | Bauer |
| 5,611,515 A | 3/1997 | Benderev et al. |
| 5,620,461 A | 4/1997 | Moer et al. |
| 5,626,614 A | 5/1997 | Hart |
| 5,630,824 A | 5/1997 | Hart |
| 5,643,321 A | 7/1997 | McDevitt |
| 5,647,836 A | 7/1997 | Blake et al. |
| 5,653,373 A | 8/1997 | Green et al. |
| 5,665,109 A | 9/1997 | Yoon |
| 5,667,486 A | 9/1997 | Mikulich et al. |
| 5,667,488 A | 9/1997 | Lundquist et al. |
| 5,667,522 A | 9/1997 | Flomenblit et al. |
| 5,669,917 A | 9/1997 | Sauer et al. |
| 5,672,171 A | 9/1997 | Andrus et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,775,328 A | 7/1998 | Lowe et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,941,439 A | 8/1999 | Kammerer et al. |
| 5,944,739 A | 8/1999 | Zlock et al. |
| 5,948,000 A | 9/1999 | Larsen et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,024,751 A | 2/2000 | Lovato et al. |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,053,935 A | 4/2000 | Brenneman et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,156,044 A | 12/2000 | Kammerer et al. |
| 6,156,049 A | 12/2000 | Lovato et al. |
| 6,159,207 A | 12/2000 | Yoon |
| 6,159,234 A | 12/2000 | Bonutti et al. |
| 6,193,714 B1 | 2/2001 | McGaffigan et al. |
| 6,200,329 B1 | 3/2001 | Fung et al. |
| 6,203,565 B1 | 3/2001 | Bonutti et al. |
| 6,206,895 B1 | 3/2001 | Levinson |
| 6,206,907 B1 | 3/2001 | Marino et al. |
| 6,228,096 B1 | 5/2001 | Marchand |
| 6,235,024 B1 | 5/2001 | Tu |
| 6,258,124 B1 | 7/2001 | Darois et al. |
| 6,261,302 B1 | 7/2001 | Voegele et al. |
| 6,261,320 B1 | 7/2001 | Tam et al. |
| 6,270,530 B1 | 8/2001 | Eldridge et al. |
| 6,280,441 B1 | 8/2001 | Ryan |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,295,990 B1 | 10/2001 | Lewis et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,387,041 B1 | 5/2002 | Harari et al. |
| 6,398,795 B1 | 6/2002 | McAlister et al. |
| 6,398,796 B2 | 6/2002 | Levinson |
| 6,425,900 B1 | 7/2002 | Knodel et al. |
| 6,425,919 B1 | 7/2002 | Lambrecht |
| 6,428,538 B1 | 8/2002 | Blewett et al. |
| 6,428,562 B2 | 8/2002 | Bonutti |
| 6,436,107 B1 | 8/2002 | Wang et al. |
| 6,461,355 B2 | 10/2002 | Svejkovsky et al. |

(56) References Cited

U.S. PATENT DOCUMENTS

| | | |
|---|---|---|
| 6,482,235 B1 | 11/2002 | Lambrecht et al. |
| 6,488,691 B1 | 12/2002 | Carroll et al. |
| 6,491,672 B2 | 12/2002 | Slepian et al. |
| 6,491,707 B2 | 12/2002 | Makower et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,514,247 B1 | 2/2003 | McGaffigan et al. |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,530,933 B1 | 3/2003 | Yeung et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,595,911 B2 | 7/2003 | LoVuolo |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,638,275 B1 | 10/2003 | McGaffigan et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,716,252 B2 | 4/2004 | Lazarovitz et al. |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,770,101 B2 | 8/2004 | Desmond, III et al. |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,790,223 B2 | 9/2004 | Reever |
| 6,802,838 B2 | 10/2004 | Loeb et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,988,983 B2 | 1/2006 | Connors et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,004,965 B2 | 2/2006 | Gross |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,065,325 B2 | 6/2006 | Zegelin et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,096,301 B2 | 8/2006 | Beaudoin et al. |
| 7,104,949 B2 | 9/2006 | Anderson et al. |
| 7,105,004 B2 | 9/2006 | DiCesare et al. |
| 7,108,655 B2 | 9/2006 | Whalen et al. |
| 7,112,226 B2 | 9/2006 | Gellman |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,335,197 B2 | 2/2008 | Sage et al. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,437,194 B2 | 10/2008 | Skwarek et al. |
| 7,463,934 B2 | 12/2008 | Tronnes et al. |
| 7,470,228 B2 | 12/2008 | Connors et al. |
| 7,481,771 B2 | 1/2009 | Fonseca et al. |
| 7,485,124 B2 | 2/2009 | Kuhns et al. |
| 7,553,317 B2 | 6/2009 | William et al. |
| 7,608,108 B2 | 10/2009 | Bhatnagar et al. |
| 7,632,297 B2 | 12/2009 | Gross |
| 7,645,286 B2 | 1/2010 | Catanese et al. |
| 7,658,311 B2 | 2/2010 | Boudreaux |
| 7,666,197 B2 | 2/2010 | Orban |
| 7,674,275 B2 | 3/2010 | Martin et al. |
| 7,682,374 B2 | 3/2010 | Foerster et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,731,725 B2 | 6/2010 | Gadberry et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,780,687 B2 | 8/2010 | Heinrich et al. |
| 7,794,494 B2 | 9/2010 | Sahatjian et al. |
| 7,815,655 B2 | 10/2010 | Catanese et al. |
| 7,850,712 B2 | 12/2010 | Conlon et al. |
| 7,862,542 B1 | 1/2011 | Harmon |
| 7,862,584 B2 | 1/2011 | Lyons et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,905,904 B2 | 3/2011 | Stone et al. |
| 7,909,836 B2 | 3/2011 | McLean et al. |

(56) References Cited

U.S. PATENT DOCUMENTS

| | | |
|---|---|---|
| 7,914,542 B2 | 3/2011 | Lamson et al. |
| 7,922,645 B2 | 4/2011 | Kaplan |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese et al. |
| 8,162,960 B2 | 4/2012 | Manzo |
| 8,167,830 B2 | 5/2012 | Noriega |
| 8,211,118 B2 | 7/2012 | Catanese et al. |
| 8,216,254 B2 | 7/2012 | McLean et al. |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng et al. |
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei et al. |
| 8,419,723 B2 | 4/2013 | Shadduck et al. |
| 8,425,535 B2 | 4/2013 | McLean et al. |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong et al. |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,758,366 B2 | 6/2014 | McLean et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,402,711 B2 | 8/2016 | Catanese et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,549,739 B2 | 1/2017 | Catanese et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 9,931,192 B2 | 4/2018 | McLean et al. |
| 10,130,353 B2 | 11/2018 | Catanese et al. |
| 10,426,509 B2 | 10/2019 | Merrick et al. |
| 10,702,261 B2 | 7/2020 | Stiggelbout |
| 11,331,093 B2 | 5/2022 | Catanese et al. |
| 11,471,148 B2 | 10/2022 | Lamson et al. |
| 11,504,149 B2 | 11/2022 | Merrick et al. |
| 11,672,520 B2 | 6/2023 | Lamson et al. |
| 11,850,140 B2 | 12/2023 | Lamson |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0151967 A1 | 10/2002 | Mikus et al. |
| 2002/0161382 A1 | 10/2002 | Neisz et al. |
| 2002/0177866 A1 | 11/2002 | Weikel et al. |
| 2002/0183740 A1 | 12/2002 | Edwards et al. |
| 2002/0193809 A1 | 12/2002 | Meade et al. |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery et al. |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0229263 A1 | 12/2003 | Connors et al. |
| 2003/0236535 A1 | 12/2003 | Onuki et al. |
| 2004/0010301 A1 | 1/2004 | Kindlein et al. |
| 2004/0030217 A1 | 2/2004 | Yeung et al. |
| 2004/0043052 A1 | 3/2004 | Hunter et al. |
| 2004/0044350 A1 | 3/2004 | Martin et al. |
| 2004/0078046 A1 | 4/2004 | Barzell et al. |
| 2004/0092978 A1 | 5/2004 | Surti |
| 2004/0122456 A1 | 6/2004 | Saadat et al. |
| 2004/0122474 A1 | 6/2004 | Gellman et al. |
| 2004/0143343 A1 | 7/2004 | Grocela |
| 2004/0147958 A1 | 7/2004 | Lam et al. |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0181235 A1 | 9/2004 | Daignault et al. |
| 2004/0193191 A1 | 9/2004 | Starksen et al. |
| 2004/0193194 A1 | 9/2004 | Aufer et al. |
| 2004/0193196 A1 | 9/2004 | Appling et al. |
| 2004/0194790 A1 | 10/2004 | Laufer et al. |
| 2004/0215179 A1 | 10/2004 | Swoyer et al. |
| 2004/0215181 A1 | 10/2004 | Christopherson et al. |
| 2004/0225305 A1 | 11/2004 | Ewers et al. |
| 2004/0230316 A1 | 11/2004 | Cioanta et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0013805 A1 | 1/2005 | Tavori |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen et al. |

(56) References Cited

U.S. PATENT DOCUMENTS

| | | |
|---|---|---|
| 2005/0080454 A1 | 4/2005 | Drews et al. |
| 2005/0101982 A1 | 5/2005 | Ravenscroft et al. |
| 2005/0107811 A1 | 5/2005 | Starksen et al. |
| 2005/0107812 A1 | 5/2005 | Starksen et al. |
| 2005/0137716 A1 | 6/2005 | Gross |
| 2005/0154401 A1 | 7/2005 | Weldon et al. |
| 2005/0165272 A1 | 7/2005 | Okada et al. |
| 2005/0171522 A1 | 8/2005 | Christopherson |
| 2005/0177181 A1 | 8/2005 | Kagan et al. |
| 2005/0192652 A1 | 9/2005 | Cioanta et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0222557 A1 | 10/2005 | Baxter et al. |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251206 A1 | 11/2005 | Maahs et al. |
| 2005/0256530 A1 | 11/2005 | Petros |
| 2005/0267405 A1 | 12/2005 | Shah |
| 2005/0273138 A1 | 12/2005 | To et al. |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0020327 A1 | 1/2006 | Lashinski et al. |
| 2006/0025750 A1 | 2/2006 | Starksen et al. |
| 2006/0025784 A1 | 2/2006 | Starksen et al. |
| 2006/0025789 A1 | 2/2006 | Aufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0079880 A1 | 4/2006 | Sage et al. |
| 2006/0079881 A1 | 4/2006 | Christopherson et al. |
| 2006/0089636 A1 | 4/2006 | Christopherson et al. |
| 2006/0089646 A1 | 4/2006 | Bonutti |
| 2006/0095058 A1 | 5/2006 | Sivan et al. |
| 2006/0155308 A1 | 7/2006 | Griego |
| 2006/0167477 A1 | 7/2006 | Arcia et al. |
| 2006/0178680 A1 | 8/2006 | Nelson et al. |
| 2006/0189940 A1 | 8/2006 | Kirsch |
| 2006/0195008 A1 | 8/2006 | Whalen et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0271032 A1 | 11/2006 | Chin et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0073322 A1 | 3/2007 | Mikkaichi et al. |
| 2007/0073342 A1 | 3/2007 | Stone et al. |
| 2007/0088362 A1 | 4/2007 | Bonutti et al. |
| 2007/0100421 A1 | 5/2007 | Griffin |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0179491 A1 | 8/2007 | Kratoska et al. |
| 2007/0179496 A1 | 8/2007 | Swoyer et al. |
| 2007/0198038 A1 | 8/2007 | Cohen et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0039921 A1 | 2/2008 | Wallsten et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0221388 A1 | 9/2008 | Seibel et al. |
| 2008/0228202 A1 | 9/2008 | Cropper et al. |
| 2008/0262424 A1 | 10/2008 | Hooft |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2009/0118762 A1 | 5/2009 | Crainch et al. |
| 2009/0163934 A1 | 6/2009 | Raschdorf, Jr. et al. |
| 2009/0177288 A1 | 7/2009 | Wallsten |
| 2009/0192439 A1* | 7/2009 | Lamson ............ A61B 17/0482 600/105 |
| 2009/0198227 A1 | 8/2009 | Prakash |
| 2009/0204128 A1 | 8/2009 | Lamson et al. |
| 2010/0010631 A1 | 1/2010 | Otte et al. |
| 2010/0023022 A1 | 1/2010 | Zeiner et al. |
| 2010/0023024 A1 | 1/2010 | Zeiner et al. |
| 2010/0023025 A1 | 1/2010 | Zeiner et al. |
| 2010/0023026 A1 | 1/2010 | Zeiner et al. |
| 2010/0030262 A1 | 2/2010 | McLean et al. |
| 2010/0030263 A1 | 2/2010 | Cheng et al. |
| 2010/0049188 A1 | 2/2010 | Nelson et al. |
| 2010/0063351 A1 | 3/2010 | Witzmann et al. |
| 2010/0063542 A1 | 3/2010 | Burg et al. |
| 2010/0114162 A1 | 5/2010 | Bojarski et al. |
| 2010/0130815 A1 | 5/2010 | Gross et al. |
| 2010/0191045 A1 | 7/2010 | Gobron et al. |
| 2010/0256442 A1 | 10/2010 | Ogdahl et al. |
| 2010/0261950 A1 | 10/2010 | Lund et al. |
| 2010/0286106 A1 | 11/2010 | Gat et al. |
| 2010/0286679 A1 | 11/2010 | Hoey et al. |
| 2010/0286717 A1 | 11/2010 | Heinrich et al. |
| 2010/0298948 A1 | 11/2010 | Hoey et al. |
| 2010/0324669 A1 | 12/2010 | Hlavka et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0077676 A1 | 3/2011 | Sivan et al. |
| 2011/0082471 A1 | 4/2011 | Holcomb et al. |
| 2011/0105841 A1 | 5/2011 | Kutikov et al. |
| 2011/0144423 A1 | 6/2011 | Tong et al. |
| 2011/0152839 A1 | 6/2011 | Cima et al. |
| 2011/0160747 A1 | 6/2011 | McLean et al. |
| 2011/0166564 A1 | 7/2011 | Merrick et al. |
| 2011/0172755 A1 | 7/2011 | Nelson et al. |
| 2011/0190758 A1 | 8/2011 | Lamson et al. |
| 2011/0196393 A1 | 8/2011 | Eliachar et al. |
| 2011/0202052 A1 | 8/2011 | Gelbart et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2011/0276086 A1 | 11/2011 | Al-Qbandi et al. |
| 2012/0010645 A1 | 1/2012 | Feld |
| 2012/0041533 A1 | 2/2012 | Bertolino et al. |
| 2012/0041534 A1 | 2/2012 | Clerc et al. |
| 2012/0059387 A1 | 3/2012 | Schanz et al. |
| 2012/0165837 A1 | 6/2012 | Belman et al. |
| 2012/0203250 A1 | 8/2012 | Weir et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0178871 A1 | 7/2013 | Koogle et al. |

(56) References Cited

U.S. PATENT DOCUMENTS

| | | |
|---|---|---|
| 2013/0197547 A1 | 8/2013 | Fukuoka et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |
| 2014/0005690 A1 | 1/2014 | Catanese et al. |
| 2014/0012192 A1 | 1/2014 | Bar-On et al. |
| 2014/0031835 A1 | 1/2014 | Viker et al. |
| 2014/0088587 A1 | 3/2014 | Merrick et al. |
| 2014/0180067 A1 | 6/2014 | Stigall et al. |
| 2014/0207179 A1 | 7/2014 | Farhangnia et al. |
| 2014/0221981 A1 | 8/2014 | Cima et al. |
| 2014/0236230 A1 | 8/2014 | Johnston et al. |
| 2014/0275756 A1 | 9/2014 | Bender et al. |
| 2014/0288637 A1 | 9/2014 | Clerc et al. |
| 2014/0296881 A1 | 10/2014 | Ranucci et al. |
| 2015/0025652 A1 | 1/2015 | McLean et al. |
| 2015/0112299 A1 | 4/2015 | Forbes et al. |
| 2015/0127050 A1 | 5/2015 | Lamson et al. |
| 2015/0157309 A1 | 6/2015 | Bird |
| 2015/0257908 A1 | 9/2015 | Chao et al. |
| 2015/0335393 A1 | 11/2015 | Ciulla et al. |
| 2015/0351743 A1 | 12/2015 | Stiggelbout |
| 2016/0000455 A1 | 1/2016 | Golan et al. |
| 2016/0022265 A1 | 1/2016 | Kawaura et al. |
| 2016/0038087 A1 | 2/2016 | Hunter |
| 2016/0045297 A1 | 2/2016 | Siegel et al. |
| 2016/0051735 A1 | 2/2016 | Slepian |
| 2016/0081736 A1 | 3/2016 | Hoey et al. |
| 2016/0089140 A1 | 3/2016 | Kawaura et al. |
| 2016/0095685 A1 | 4/2016 | Vemuri et al. |
| 2016/0096009 A1 | 4/2016 | Feld |
| 2016/0120647 A1 | 5/2016 | Rogers et al. |
| 2016/0206370 A1 | 7/2016 | Fruland et al. |
| 2016/0242894 A1 | 8/2016 | Davis |
| 2016/0302904 A1 | 10/2016 | Ogdahl et al. |
| 2016/0317180 A1 | 11/2016 | Kilemnik |
| 2017/0000598 A1 | 1/2017 | Bachar |
| 2017/0128741 A1 | 5/2017 | Keltner et al. |
| 2017/0135830 A1 | 5/2017 | Harkin et al. |
| 2017/0156723 A1 | 6/2017 | Keating et al. |
| 2018/0103945 A1 | 4/2018 | Ciulla et al. |
| 2018/0146964 A1 | 5/2018 | Garcia et al. |
| 2018/0318114 A1 | 11/2018 | Huang et al. |
| 2018/0353169 A1 | 12/2018 | Lamson et al. |
| 2018/0353181 A1 | 12/2018 | Wei |
| 2019/0125334 A1 | 5/2019 | Tong et al. |
| 2020/0015837 A1 | 1/2020 | Merrick et al. |
| 2020/0022692 A1 | 1/2020 | Lamson et al. |
| 2020/0038213 A1 | 2/2020 | Bly et al. |
| 2020/0121442 A1 | 4/2020 | Askeland |
| 2020/0187931 A1 | 6/2020 | Lamson et al. |
| 2021/0145619 A1 | 5/2021 | Bly et al. |
| 2021/0161641 A1 | 6/2021 | Bachar |
| 2021/0161642 A1 | 6/2021 | Jen et al. |
| 2021/0307641 A1 | 10/2021 | Rumbles et al. |
| 2021/0378659 A1 | 12/2021 | Lamson et al. |
| 2021/0378784 A1 | 12/2021 | Welch et al. |
| 2022/0000445 A1 | 1/2022 | Datta et al. |
| 2022/0031357 A1 | 2/2022 | Cutts et al. |
| 2022/0031358 A1 | 2/2022 | Yarra et al. |
| 2022/0031389 A1 | 2/2022 | Fischell et al. |
| 2022/0061834 A1 | 3/2022 | Chung et al. |
| 2022/0125499 A1 | 4/2022 | Hoey et al. |
| 2022/0133462 A1 | 5/2022 | Kilemnik |
| 2022/0142464 A1 | 5/2022 | Petroff et al. |
| 2022/0240921 A1 | 8/2022 | Catanese et al. |
| 2022/0240925 A1 | 8/2022 | Epstein et al. |
| 2022/0249219 A1 | 8/2022 | Chung et al. |
| 2022/0265262 A1 | 8/2022 | Melsheimer |
| 2022/0273918 A1 | 9/2022 | Ghriallais et al. |
| 2022/0378577 A1 | 12/2022 | Anderson et al. |
| 2022/0395363 A1 | 12/2022 | Ghriallais et al. |
| 2023/0022482 A1 | 1/2023 | Dhavale |
| 2023/0200802 A1 | 6/2023 | Catanese, III |
| 2023/0225851 A1 | 7/2023 | Lamson et al. |
| 2023/0293166 A1 | 9/2023 | Lamson et al. |

FOREIGN PATENT DOCUMENTS

| | | |
|---|---|---|
| CN | 101795641 A | 8/2010 |
| CN | 102112064 B | 6/2014 |
| CN | 105852938 A | 8/2016 |
| CN | 105919695 A | 9/2016 |
| CN | 109675177 A | 4/2019 |
| CN | 211156119 U | 8/2020 |
| CN | 112891032 A | 6/2021 |
| CN | 216221843 U | 4/2022 |
| DE | 10159470 A1 | 6/2003 |
| DE | 102019101987 A1 | 7/2020 |
| EP | 0246836 B1 | 12/1991 |
| EP | 0464480 A1 | 1/1992 |
| EP | 0274846 B1 | 2/1994 |
| EP | 0632999 A1 | 1/1995 |
| EP | 0667126 A1 | 8/1995 |
| EP | 1016377 A2 | 7/2000 |
| EP | 1482841 A1 | 12/2004 |
| EP | 1082941 B1 | 3/2005 |
| EP | 1584295 A2 | 10/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1670361 B1 | 4/2008 |
| EP | 1331886 B1 | 12/2008 |
| EP | 1482840 B1 | 12/2008 |
| EP | 2243507 A1 | 10/2010 |
| EP | 1484023 B1 | 5/2011 |
| EP | 2345373 A1 | 7/2011 |
| EP | 2345374 A1 | 7/2011 |
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| JP | 2023502729 A | 1/2023 |
| KR | 20060009698 A | 2/2006 |
| KR | 101534820 B1 | 7/2015 |
| RU | 2062121 C1 | 6/1996 |
| RU | 2112571 C1 | 6/1998 |
| RU | 2128012 C1 | 3/1999 |
| RU | 2221501 C2 | 1/2004 |
| WO | 1987001270 A1 | 3/1987 |
| WO | 1992010142 A1 | 6/1992 |
| WO | 1993004727 A1 | 3/1993 |
| WO | 1993015664 A1 | 8/1993 |
| WO | 1994026170 A1 | 11/1994 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2002058577 A1 | 8/2002 |

(56) References Cited

FOREIGN PATENT DOCUMENTS

| | | |
|---|---|---|
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004066875 A1 | 8/2004 |
| WO | 2004080529 A2 | 9/2004 |
| WO | 2004103189 A1 | 12/2004 |
| WO | 2005034738 A2 | 4/2005 |
| WO | 2005065412 A2 | 7/2005 |
| WO | 2005094447 A2 | 10/2005 |
| WO | 2006127241 A2 | 11/2006 |
| WO | 2006127431 A2 | 11/2006 |
| WO | 2007048437 A1 | 5/2007 |
| WO | 2007053516 A2 | 5/2007 |
| WO | 2007064906 A2 | 6/2007 |
| WO | 2007075981 A2 | 7/2007 |
| WO | 2008002340 A2 | 1/2008 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2008132735 A1 | 11/2008 |
| WO | 2008142677 A2 | 11/2008 |
| WO | 2009009617 A1 | 1/2009 |
| WO | 2009072131 A2 | 6/2009 |
| WO | 2010011832 A1 | 1/2010 |
| WO | 2010014821 A2 | 2/2010 |
| WO | 2010014825 A1 | 2/2010 |
| WO | 2010065214 A2 | 6/2010 |
| WO | 2010086849 A1 | 8/2010 |
| WO | 2010106543 A2 | 9/2010 |
| WO | 2011084712 A1 | 7/2011 |
| WO | 2012018446 A2 | 2/2012 |
| WO | 2012028843 A1 | 3/2012 |
| WO | 2012079548 A1 | 6/2012 |
| WO | 2012079549 A2 | 6/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |
| WO | 2012123950 A2 | 9/2012 |
| WO | 2014003987 A1 | 1/2014 |
| WO | 2014035506 A2 | 3/2014 |
| WO | 2014145381 A1 | 9/2014 |
| WO | 2014153219 A1 | 9/2014 |
| WO | 2014200764 A1 | 12/2014 |
| WO | 2015101975 A1 | 7/2015 |
| WO | 2016134166 A1 | 8/2016 |
| WO | 2017017499 A1 | 2/2017 |
| WO | 2017081326 A2 | 5/2017 |
| WO | 2017112856 A1 | 6/2017 |
| WO | 2021190092 A1 | 9/2021 |

OTHER PUBLICATIONS

Bacharova, O.A., et al. "The Effect of Rhodiolae rosea Extract on Incidence Rate of Superficial Bladder Carcinoma Relapses", Kozin 1995.
Berges, Richard, et al. "Alternative Minimalinvasive Therapien Beim Benignen Prostatasyndrom", Medizin, Jg. 104, Heft 37, Sep. 14, 2007.
Borzhievski, et al., "Tactics of the Surgical Treatment of Patients With Prostatic Adenoma and Acute Urinary Retention," Urologia Nefrol (Mosk), Jan.-Feb. 1987, (1):39-43.
European Search Report for EP Application No. 06770621.8, mailed Sep. 20, 2012.
European Search Report for EP Application No. 06845991.6, mailed on Mar. 22, 2013.
European Search Report for EP Application No. 07840462.1, mailed May 29, 2012.
European Search Report for EP Application No. 08729001.1, mailed on Feb. 4, 2014.
European Search Report for EP Application No. 08772483.7, mailed on Feb. 12, 2015.
European Search Report for EP Application No. 11154962.2, mailed on May 19, 2011.
European Search Report for EP Application No. 11154976.2, mailed on Jun. 6, 2011.
European Search Report for EP Application No. 11814950.9, mailed on Sept. 8, 2015.
European Search Report for EP Application No. 11852778.7, mailed on Nov. 19, 2015.
European Search Report for EP Application No. 11854148.1, mailed on Oct. 20, 2017.
European Search Report for EP Application No. 13810314.8, mailed on Apr. 6, 2016.
European Search Report for EP Application No. 17150545.6, mailed on Sep. 11, 2017.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36): A 2424-9.
Hubmann, R. "Geschichte der transurethralen Prostataeingriffe", Geschichte der Medizin, Urologe [B], 2000, 40:152-160.
International Search Report for PCT Application No. PCT/US2006/019372, mailed on May 2, 2008.
International Search Report for PCT Application No. PCT/US2006/048962, mailed Dec. 10, 2008.
International Search Report for PCT Application No. PCT/US2007/074019, mailed on Jul. 25, 2008.
International Search Report for PCT Application No. PCT/US2008/053001, mailed on Jun. 17, 2008.
International Search Report for PCT Application No. PCT/US2008/069560, mailed on Sep. 8, 2008.
International Search Report for PCT Application No. PCT/US2009/052271, mailed on Apr. 7, 2010.
International Search Report for PCT Application No. PCT/US2009/052275, mailed on Oct. 9, 2009.
International Search Report for PCT Application No. PCT/US2011/041200, mailed on Feb. 17, 2012.
International Search Report for PCT Application No. PCT/US2011/065348, mailed on Jun. 21, 2012.
International Search Report for PCT Application No. PCT/US2011/065358, mailed on Jun. 21, 2012.
International Search Report for PCT Application No. PCT/US2011/065377, mailed on Aug. 29, 2012.
International Search Report for PCT Application No. PCT/US2011/065386, mailed on Jun. 28, 2012.
International Search Report for PCT Application No. PCT/US2013/044035, mailed on Sept. 6, 2013.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
PCT International Search Report and Written Opinion mailed Mar. 19, 2019, in PCT/US2018/067229.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Trapeznikov, et al., "New Technologies in the Treatment of Benign Prostatic Hyperplasia", Urologia Nefrol (Mosk), Jul.-Aug. 1996, (4):41-47.
Written Opinion mailed Sep. 13, 2021 in Singapore Patent Application No. 11202005766X.

(56) References Cited

OTHER PUBLICATIONS

Yeung, Jeff. "Treating Urinary Stress Incontenance Without Incision with Endoscopic Suture Anchor & Approximating Device," Aleeva Medical, Inc., 2007.
Singapore Search Report and Written Opinion mailed Apr. 11, 2024, in Singapore Patent Application No. 10202251621P.

* cited by examiner

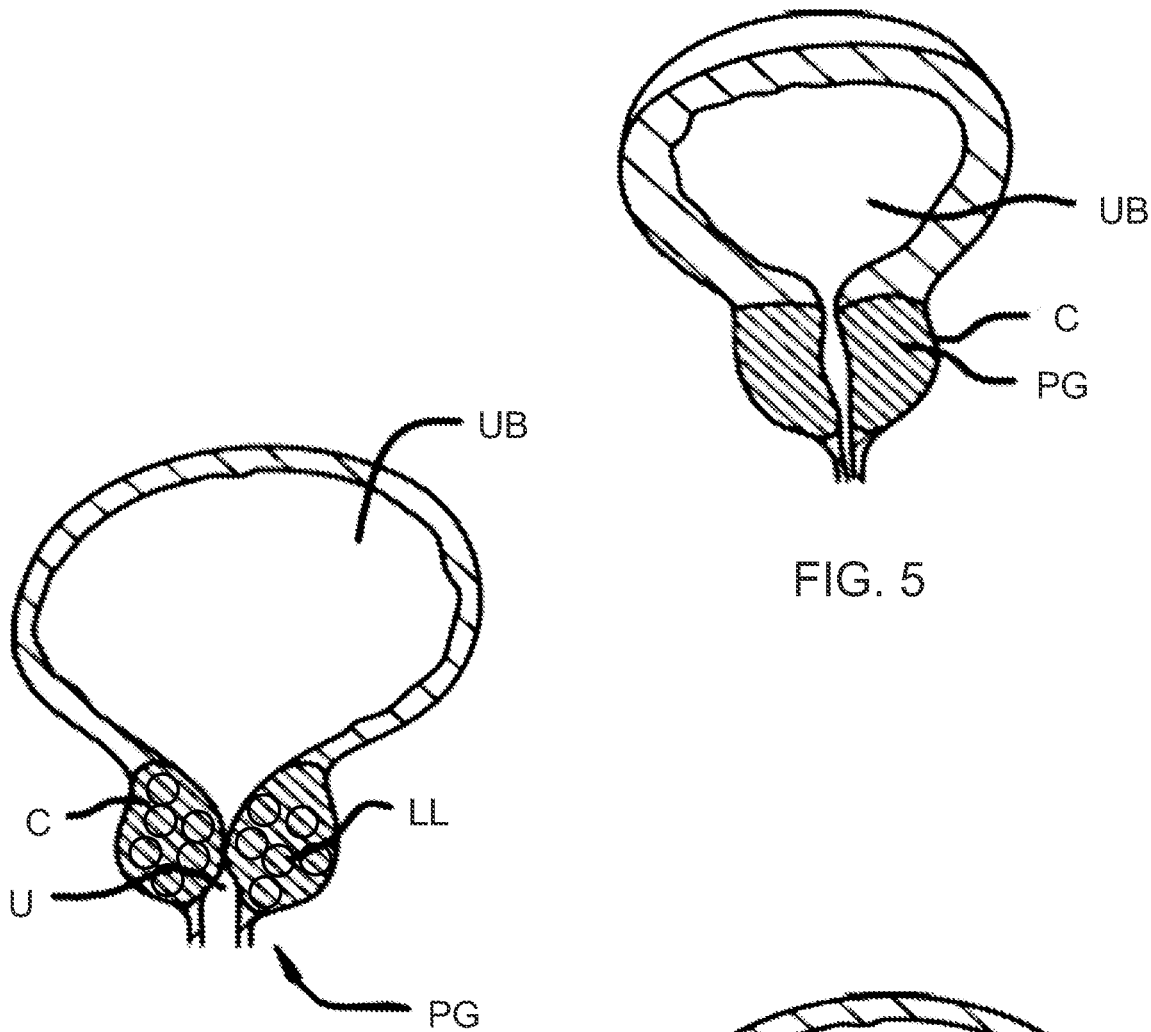
FIG. 5
FIG. 6
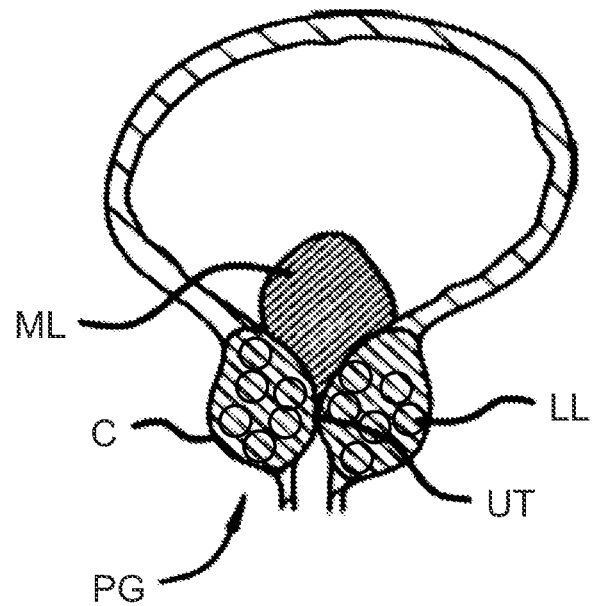
FIG. 7

Section A-A

EXPANDABLE TISSUE ENGAGEMENT APPARATUS AND METHOD

CROSS REFERENCE TO RELATED APPLICATIONS

This application is a continuation of U.S. application Ser. No. 16/577,013 filed Sep. 20, 2019, now U.S. Pat. No. 11,672,520, which is a continuation of PCT Application Serial No. PCT/US18/67229 filed Dec. 21, 2018, which claims priority to U.S. Provisional Application Ser. No. 62/610,184, filed Dec. 23, 2017, entitled "Median Lobe Engagement Apparatus and Method," each of which is incorporated herein by reference.

FIELD OF THE DISCLOSURE

The present disclosure relates generally to medical devices and methods, and more particularly to systems and associated methods for manipulating or engaging tissues and anatomical or other structures within the body of human or animal subjects for the purpose of treating diseases or disorders.

One example of a condition where it is desirable to lift, compress, or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra as a result of the gland enlarging. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and hypertrophy and stiffness of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, and urgent need to urinate.

In addition to being present in patients with BPH, LUTS may also be present in patients with prostate cancer, prostate infections, and chronic use of certain medications (e.g. ephedrine, pseudoephedrine, phenylpropanolamine, and antihistamines such as diphenhydramine or chlorpheniramine) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery, and minimally invasive procedures.

For patients who choose the watchful waiting option, no immediate treatment is provided to the patient, but the patient undergoes regular exams to monitor progression of the disease. This is usually done on patients who have minimal symptoms that are not especially bothersome.

Medical procedures for treating BPH symptoms include Transurethal Resection of the Prostate (TURP), Transurethral Electrovaporization of the Prostate (TVP), Transurethral Incision of the Prostate (TUIP), Laser Prostatectomy, Open Prostatectomy, Transurethral Microwave Thermotherapy (TUMT), Transurethral Needle Ablation (TUNA), Interstitial Laser Coagulation (ILC), and Prostatic Stents.

The most effective current methods of treating BPH in terms of relieving the symptoms of BPH also carry a high risk of adverse effects. These methods may require general or spinal anesthesia and/or may have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and, in fact, often experiences worse symptoms for weeks after the procedure until the body begins to heal. Additionally, many surgical or minimally invasive approaches require a urethral catheter to be placed in the bladder, and in some cases left in the bladder for weeks. In some cases, catheterization is indicated because the therapy actually causes obstruction during a period of time post operatively, and in other cases it is indicated because of post-operative bleeding and the potential for the formation of occlusive clots. While drug therapies are easy to administer, the results are frequently suboptimal, take significant time to take effect, and often include undesirable side effects.

There have been advances in developing minimally invasive devices and methods for displacing and/or compress lobes of a prostate gland to receive pressure on and provide a less obstructed path through a urethra. These methods have focused on treating the lateral lobes of the prostate gland. There remains, however, a need for the development of new devices and methods that can be used for various procedures where it is desired to lift, compress, support, or reposition the median lobe of a prostate in a discrete procedure or in combination with treating BPH. In particular, there is a need for alternative apparatus and treatment approaches for the purpose of manipulating the median lobe of a prostate.

Still further, there is an ongoing need in the field of minimally invasive medical devices for devices and methods for the manipulation of tissue in other parts of the anatomy.

The present disclosure addresses these and other needs.

SUMMARY

Embodiments of the invention include a treatment device for engaging and manipulating a median lobe of a prostate gland. The treatment device includes an elongate tissue access assembly coupled to a handle assembly, wherein the elongate tissue access assembly is configured to be inserted within an introducer sheath, and a tissue engagement structure attached to a distal end portion of the elongate tissue access assembly, wherein the tissue engagement structure can transition from a contracted state to an expanded state when the elongate tissue access assembly exits a distal end of the introducer sheath.

In another embodiment of the invention, the tissue engagement structure comprises a first expandable portion having an asymmetrical cross-section. In another embodiment of the invention, a proximal portion of the first expandable portion is attached to the elongate tissue access assembly. In another embodiment of the invention, the tissue engagement structure comprises a channel to receive the distal end portion of the elongate tissue access assembly. In another embodiment of the invention, movement of the tissue engagement structure relative to the elongate tissue access assembly is constrained to be along a longitudinal axis of the elongate tissue access assembly. In another embodiment of the invention, movement of the tissue engagement structure relative to the elongate tissue access assembly transitions the tissue engagement structure from the contracted state to the expanded state. In another embodiment of the invention, the elongate tissue access assembly further comprises an aperture and a needle assembly that is extendable through the aperture. In another embodiment of the invention, the tissue engagement structure further comprises a first visual marker indicating a tissue entry position for the needle assembly. In another embodiment of the invention, the tissue engagement structure further comprises a second expandable portion having an asymmetrical cross-section. In another embodiment of the invention, wherein the elongate tissue access assembly further comprises an aperture and a needle assembly that is extendable through the aperture.

Embodiments of the invention include, a system for engaging and manipulating a median lobe of a prostate gland such that the system includes an anchor delivery device comprising an elongate tissue access assembly, wherein the elongate tissue access assembly is configured to be inserted within an introducer sheath, a tissue anchor housed within the anchor delivery device, and a tissue engagement structure attached to a distal end portion of the elongate tissue access assembly, wherein the tissue engagement structure can transition from a contracted state to an expanded state. In another embodiment of the invention, the tissue engagement structure comprises a first expandable portion having an asymmetrical cross-section. In another embodiment of the invention, a proximal portion of the first expandable portion is fixedly attached to the elongate tissue access assembly. In another embodiment of the invention, the tissue engagement structure comprises a slidable portion coupled to the elongate tissue access assembly. In another embodiment of the invention, movement of the tissue engagement structure relative to the elongate tissue access assembly transitions the tissue engagement structure from the contracted state to the expanded state. In another embodiment of the invention, the anchor delivery device further comprises a needle assembly. In another embodiment of the invention, the needle assembly is configured to deliver the tissue anchor. In another embodiment of the invention, the tissue engagement structure comprises a first expandable portion. In another embodiment of the invention, the first expandable portion further comprises a first visual marker indicating a tissue entry position for the needle assembly. In another embodiment of the invention, the tissue engagement structure further comprises a second expandable portion.

Other features and advantages of the present disclosure will become apparent from the following detailed description, taken in conjunction with the accompanying drawings, which illustrate, by way of example, the principles of the disclosure.

BRIEF DESCRIPTION OF THE DRAWINGS

FIG. 5 is a cross-sectional view, depicting a normal prostate.

FIG. 6 is a cross-sectional view, depicting a prostate with enlarged lateral lobes.

FIG. 7 is a cross-sectional view, depicting a prostate with enlarged lateral lobes and an enlarged median lobe.

DETAILED DESCRIPTION OF THE SEVERAL DRAWINGS

Turning now to the figures, which are provided by way of example and not limitation, the present disclosure is directed to a device configured to engage and manipulate tissue within a patient's body for treatment purposes. The disclosed apparatus can be employed for various medical purposes including but not limited to retracting, lifting, compressing, approximating, supporting, and/or repositioning tissues, organs, anatomical structures, grafts, or other material found within a patient's body. Such tissue manipulation is intended to facilitate the treatment of diseases or disorders, including, but not limited to, the displacement, compression and/or retraction of the median lobe of a prostate.

In an aspect of the present disclosure, the tissue engagement or manipulation forms the primary interventional procedure. In other aspects, the tissue engagement or manipulation forms one portion of an interventional procedure, such as the treatment of BPH or for the purpose of retracting, lifting, compressing, approximating, supporting or repositioning other anatomy or for the purpose of retracting, lifting, compressing, approximating, supporting, or repositioning a first section of anatomy with respect to a second section of anatomy.

With reference to FIGS. 1-4, various features of urological anatomy of a human male subject are presented. The prostate gland PG is a walnut-sized gland located adjacent the urinary bladder UB. The urethra UT runs through the prostate gland PG and the penis P. The prostate gland PG secretes fluid that protects and nourishes sperm. The prostate gland PG also contracts during ejaculation to expel semen and to provide a valve to keep urine out of the semen. A capsule C surrounds the prostate gland PG.

The urinary bladder UB holds urine. The vas deferentia VD define ducts through which semen is carried, and the seminal vesicles SV secrete seminal fluid. The rectum R is the end segment of the large intestine through which waste is dispelled. The urethra UT carries both urine and semen out of the body. Thus, the urethra is connected to the urinary bladder UB and provides a passageway to the vas deferentia VD and seminal vesicles SV. The verumontanum VM is a crest in the wall of the urethra UT where the seminal ducts enter. The prostatic urethra is the section of the urethra UT which extends through the prostate. The trigone T (see FIG. 3) is a smooth triangular region of the bladder. It is sensitive to expansion and signals the brain when the urinary bladder UB is full.

Figure 1:
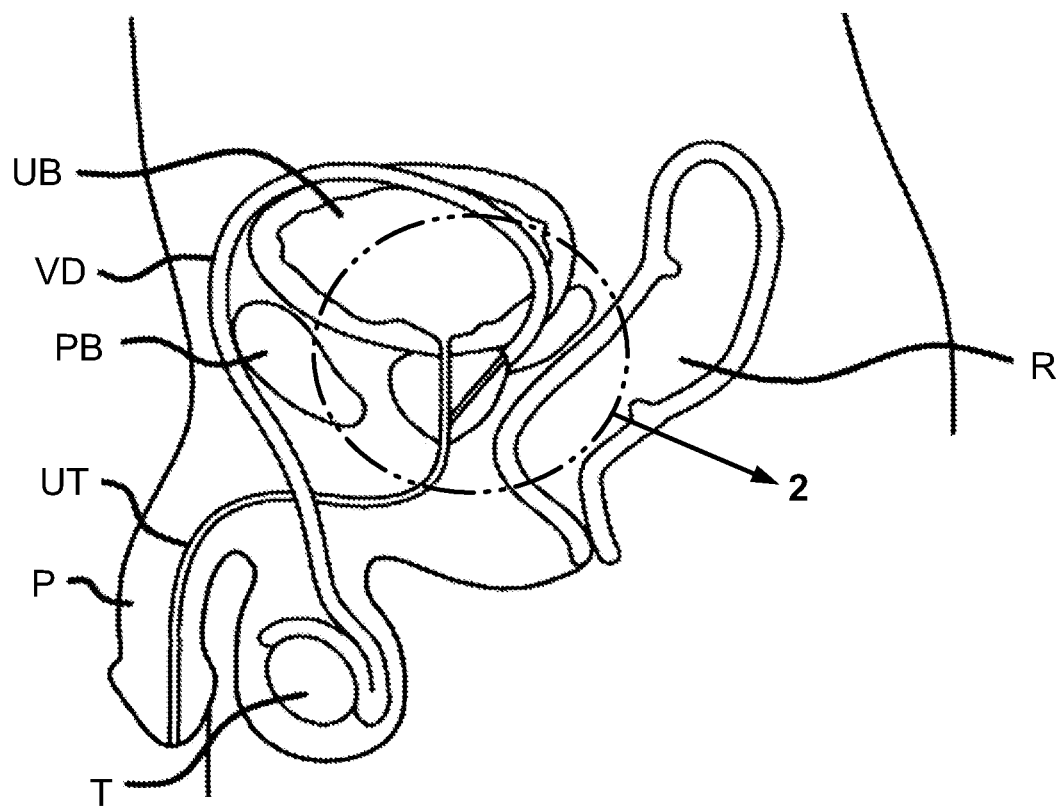
FIG. 1 is a cross-sectional view, depicting anatomy in the area surrounding a prostate in a human subject.
Figure 2:
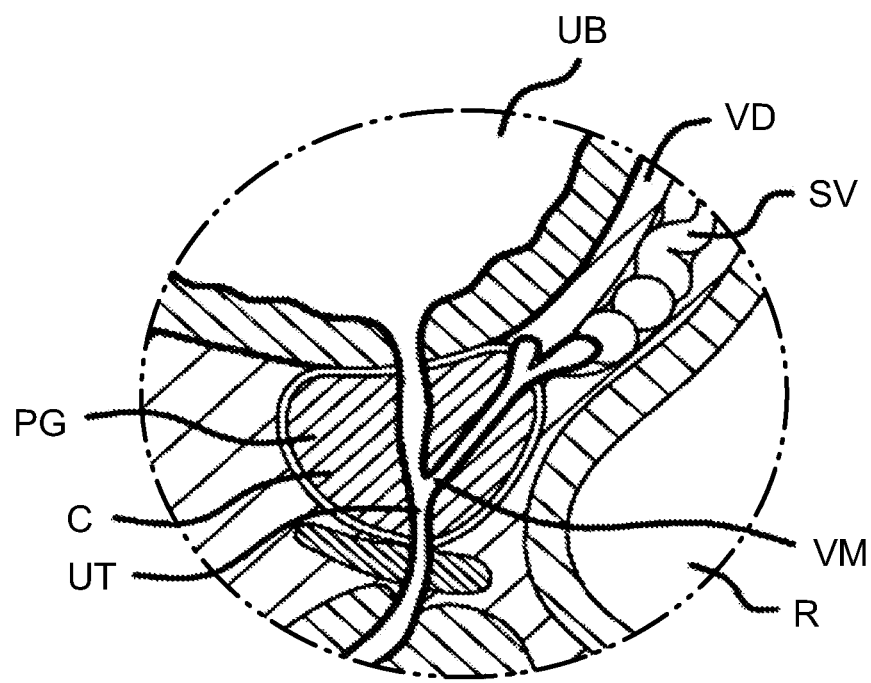
FIG. 2 is an enlarged cross-sectional view of an area of FIG. 1, depicting anatomy immediately surrounding and adjacent a prostate.
Figure 3:
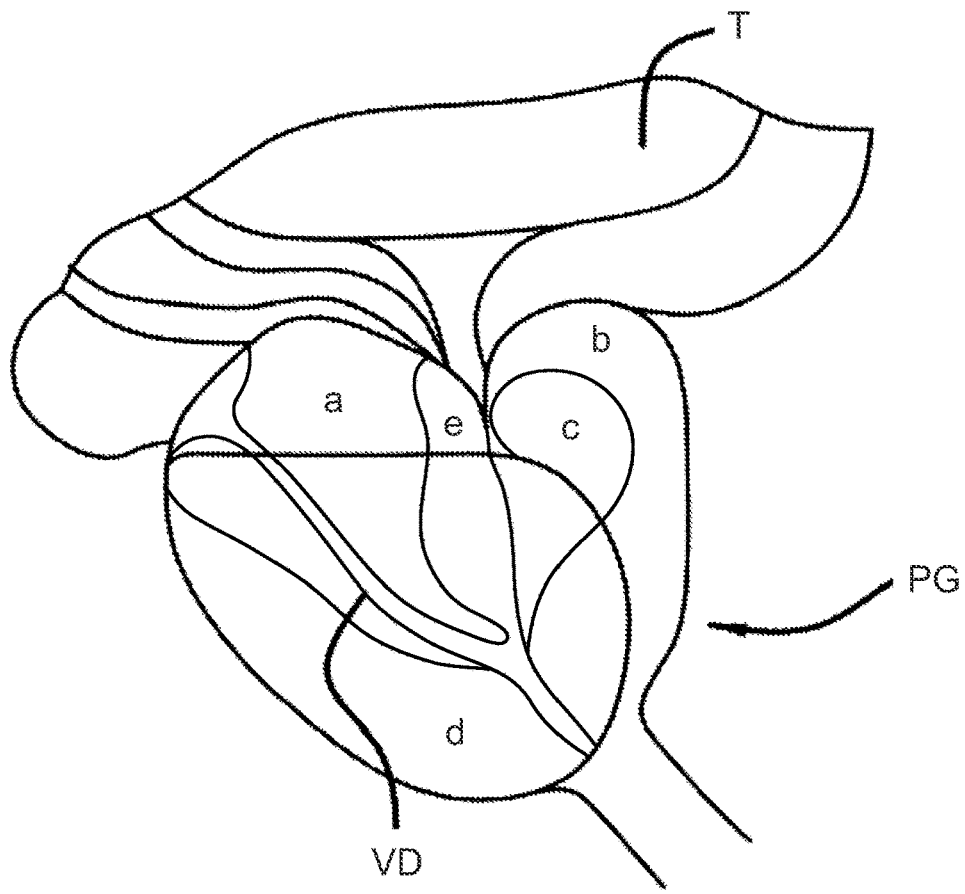
FIG. 3 is a schematic view, depicting prostatic anatomy zones.
Figure 4:
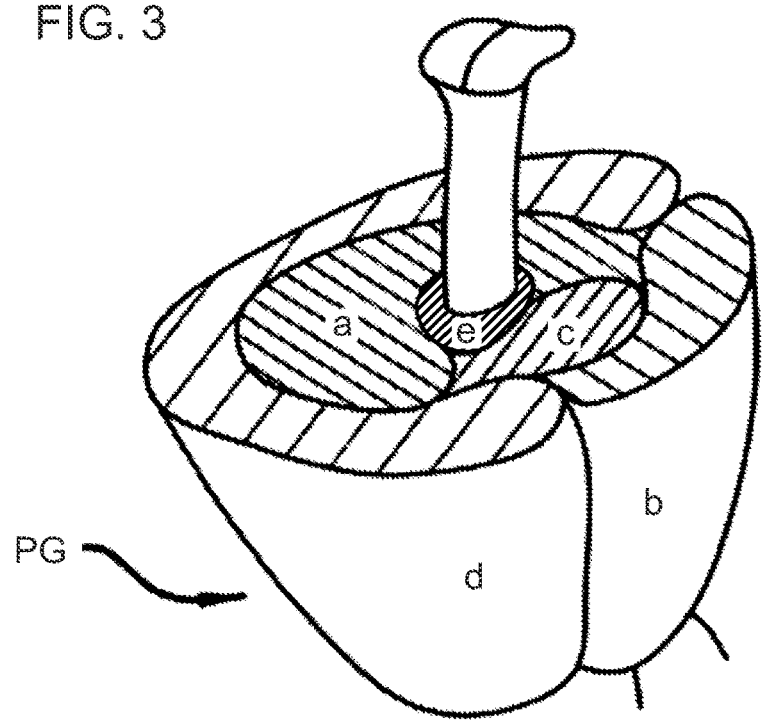
FIG. 4 is a schematic cross-sectional view, depicting further details of the anatomy zones shown in FIG. 3.

The prostate gland can be classified by zones or described by referring to its lobes (See FIG. 4). Whereas the zone classification is typically used in pathology, the lobe classification is more often used in anatomy. The central zone (a) of a prostate gland PG is about 25% of a normal prostate and this zone surrounds the ejaculating ducts. There is some prevalence of benign prostate hyperplasia in the transition zone. The fibromuscular zone (b) is usually devoid of glandular components and, as its name suggests, is composed of muscle tissue and fibrous tissue. The transitional zone (c) generally overlays the proximal urethra and is the region of the gland that grows throughout life. This zone is often associated with the condition of benign prostatic enlargement. Finally, the peripheral zone (d) is the subcapsular portion of the posterior aspect of the prostate gland that surrounds the distal urethra.

The lobe characterization is different from the zone characterization, but there is some overlap. The anterior lobe is devoid of glandular tissue and is formed of fibromuscular tissue. The anterior lobe roughly corresponds to the anterior portion of the transitional zone (c). The posterior lobe roughly corresponds to the peripheral zone (d) and can be palpated through the rectum during a digital rectal exam.

The posterior lobe is the site of 70-80% of prostatic cancers. The lateral lobes are the main mass of the prostate and are separated by the urethra. All pathological zones may be present in the lateral lobes. Lastly, the median lobe roughly corresponds to part of the central zone. It varies greatly in size from subject to subject and in some cases is devoid of glandular tissue.

A large or enlarged median lobe can act as a ball valve, blocking the bladder neck, or opening, into the urethra. Various approaches are contemplated to address such a condition. It is contemplated that the median lobe can be compressed, displaced and/or retracted to eliminate or decrease the blocking of the bladder neck opening.

Turning now to FIGS. 5-7, there are shown various prostate glands in cross-section. FIG. 5 depicts the urinary bladder UB and prostate gland PG of a healthy subject. FIG. 6 illustrates an individual with a prostate having enlarged lateral lobes LL and FIG. 7 depicts a subject suffering from both enlarged lateral lobes LL and an enlarged median lobe ML. It is to be appreciated that such enlarged anatomy impinges on the urethra UT and affects normal bladder functioning. The following devices and approaches can be employed to access and manipulate prostatic tissue during an interventional or diagnostic procedure.

Figure 8A:
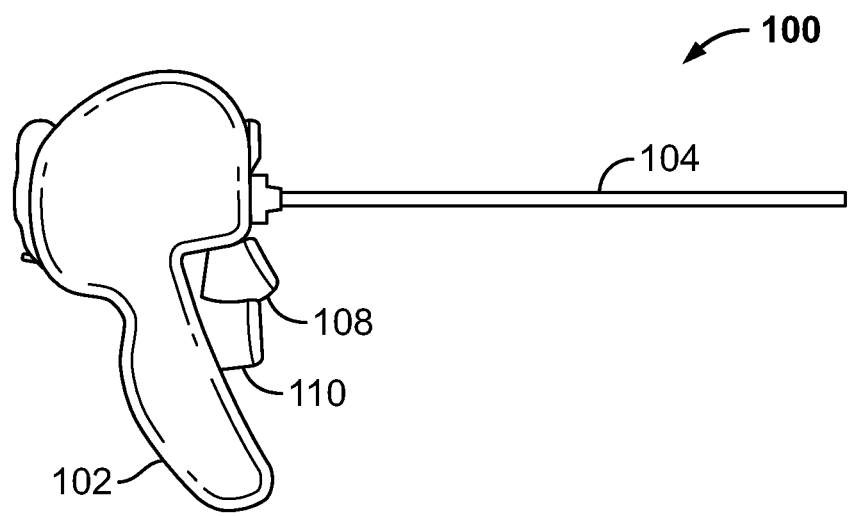
FIG. 8A is a side view, depicting an embodiment of a delivery device.
Figure 8B:
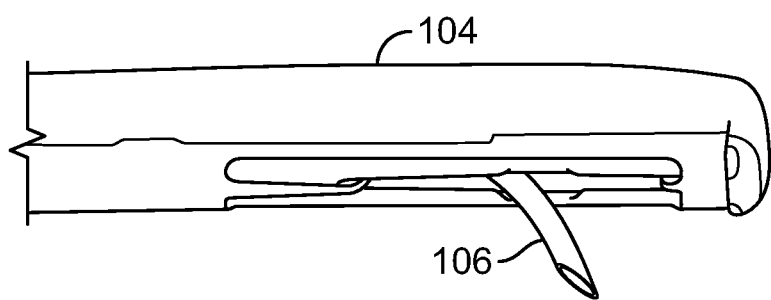
FIG. 8B is an enlarged perspective view, depicting the distal end of an embodiment of a delivery device.

Referring now to FIGS. 8A & 8B, an embodiment of a treatment device 100 is shown. Treatment device 100 can include a handle assembly 102 and an elongate tissue access assembly 104. Elongate assembly 104 can be configured to access an interventional site as well as engage and manipulate target tissue. Treatment device 100 can be configured to assemble and implant one or more anchor assemblies or implants within a patient's body. The device is further contemplated to be compatible for use with minimally invasive techniques (such as cystoscopy) such that a patient can tolerate a procedure while awake or under light sedation rather than under general anesthesia. The device additionally includes structures configured to receive a conventional remote viewing device (e.g., an endoscope) so that the steps being performed at the interventional site can be observed by the physician.

The elongate assembly 104 can house members to manipulate target tissue including, but not limited to, a needle assembly 106. Elongate assembly 104 can also be equipped with features to manipulate target tissue and/or stabilize the device at its interventional site. Elongate assembly 104 can be inserted through a sheath of a size compatible with conventional cystoscopy, including sizes such as 19F or 21F. Elongate assembly 104 can be rigid or flexible. In some preferred embodiments, elongate assembly 104 is sufficiently rigid (or can be made sufficiently rigid when at the interventional site) to allow manual compression of tissue at an interventional site by leveraging or pushing handle assembly 102. Various embodiments of treatment device 100 can include subassemblies and components to dissect, resect, or otherwise alter a prostatic lobe.

In one particular, non-limiting use in treating a prostate, the elongate tissue access assembly of a delivery device is placed within a urethra leading to a urinary bladder of a patient. In one approach, the delivery device can be placed within an introducer sheath previously positioned in the urethra or alternatively, the delivery device can be inserted directly within the urethra. When employing an introducer sheath, the sheath can be attached to a sheath mount assembly. The sheath is advanced within the patient until a leading end thereof reaches a prostate gland. In a specific approach, a first side (i.e., lateral lobe) of the prostate to be treated is chosen while the device extends through the bladder and the device is turned accordingly. The distal end of the elongate tissue access assembly can be used to depress the urethra into the prostate gland by compressing the inner prostate tissue. The inside of the prostate gland (i.e., adenoma) is spongy and compressible and the outer surface (i.e., capsule) of the prostate gland is firm. By pivoting the elongate tissue access assembly laterally about the pubic symphysis PS relative to the patient's midline, the physician can depress the urethra into the prostate gland compressing the adenoma and creating the desired opening through the urethra. Further details and background concerning related and complementary interventional procedures are described in various U.S. patents, including U.S. Pat. Nos. 8,491,606 and 8,758,366, the entirety of the contents of which are hereby incorporated by reference.

When the treatment device is used at an interventional site, such as the median lobe of the prostate, prior to deployment of an implant or alteration of prostatic tissue the median lobe often requires manipulation into a position conducive to receiving an implant. Embodiments of a device and method of use that can position and stabilize a treatment device to better engage and manipulate target tissue, including the median lobe of the prostate, are described below. In a preferred embodiment, such a device can include a winged, expandable/collapsible structure that increases the distal surface area of the device to engage and manipulate tissue.

Figure 9A:
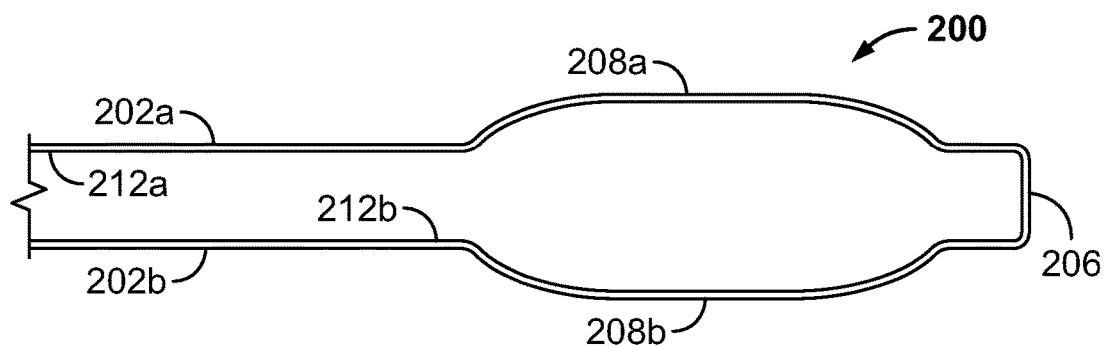
FIG. 9A is a top view, depicting an embodiment of an expandable structure that can be employed to engage and manipulate tissue.
Figure 9B:
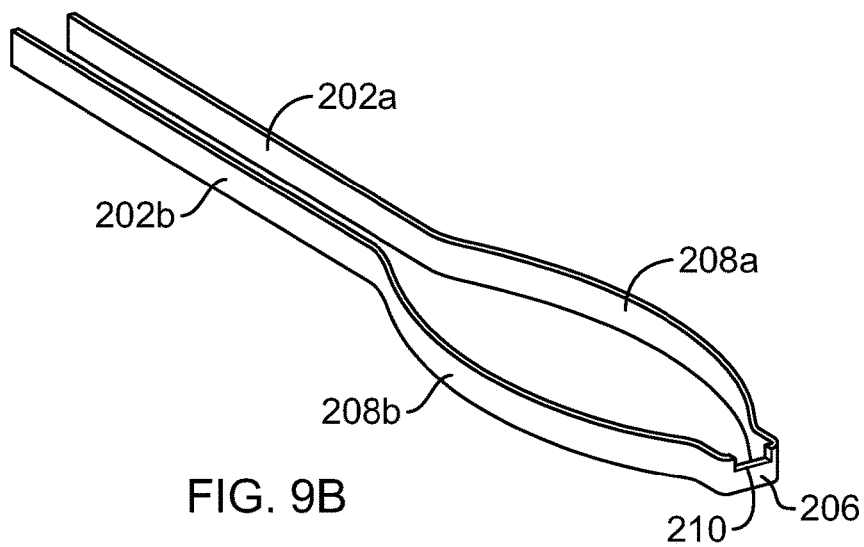
FIG. 9B is a perspective view, depicting an embodiment of an expandable structure that can be employed to engage and manipulate tissue.
Figure 9C:
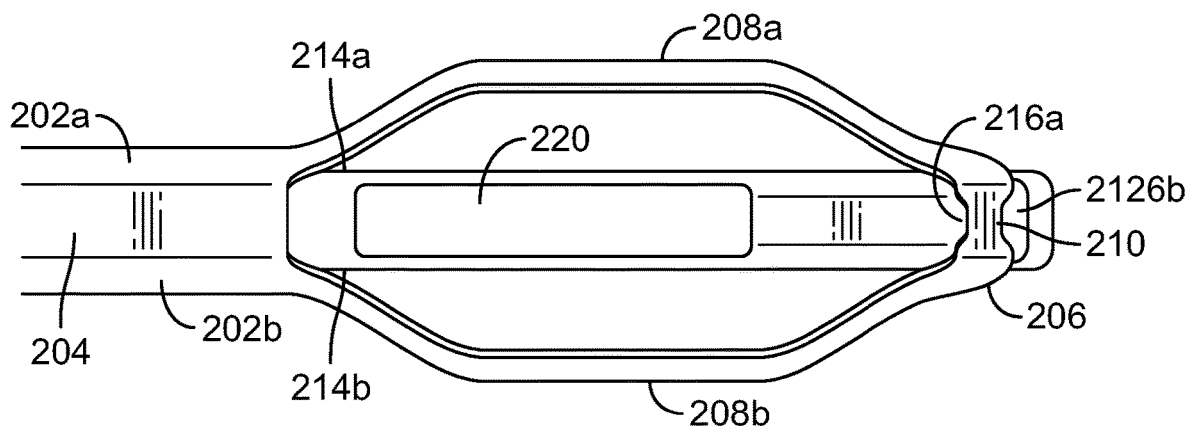
FIG. 9C is an enlarged view, depicting an embodiment of an expandable engagement and manipulation device mounted on the distal end of an embodiment of a delivery device.

FIGS. 9A-9C illustrate an expandable member 200 that can be configured for attachment to the distal end of an elongate member. Expandable member 200 can include arms 202a and 202b situated in parallel (or substantially in parallel) and connected by a distal connecting member 206 at the distal end of member 200. Each arm can have a portion that expands outward past the longitudinal axis of arms 202a and 202b. Such expandable portions can be wings 208a and 208b. In some embodiments, wings 208a and 208b can connect to form a closed loop (not shown) in place of distal connecting member 206. Distal connecting member 206 can be grooved, channeled, or otherwise hollowed to create an opening 210 formed therein.

Wings 208a and 208b can be configured to be biased to an expanded position. In this embodiment, wings 208a and 208b are moved to a retracted position by moving distal connecting member 206 and/or arms 202a and 202b in a longitudinal direction away from wings 208a and 208b. In another embodiment, wings 208a and 208b are configured in a retracted position and are moved to an expanded position by moving distal connecting member 206 and/or arms 202a and 202b in a longitudinal direction toward wings 208a and 208b. In some embodiments, each wing can be expanded or retracted independently by moving the arm on the same side as the wing in a longitudinal direction away from or toward the wing as the configuration requires.

The proximal end of expandable member 200 can be attached to an elongate tissue access assembly 204 by connecting arms 202a and 202b to the shaft of the elongate assembly. In some embodiments, elongate assembly 204 is inserted through expandable member 200 such that the inwardly-facing side 212a of arm 202a and inwardly-facing side 212b of arm 202b are flush with a portion of the outwardly-facing sides 214a and 214b of elongate assembly 204 and secured via welding or other conventional means of attachment. The distal end of expandable member 200 can interact with a portion of the distal end of elongate assembly 204. For example, opening 210 can be configured to snap into, or be otherwise secured by, elongate assembly 204. As illustrated in FIG. 9C, elongate assembly 204 can include tabs 216a and 216b removably fastened over distal connecting member 206 thereby holding the distal end of expandable member 200 in place. In some embodiments, such as when elongate assembly 204 includes an aperture 220, wings 208a and 208b can be positioned in any plane relative to the aperture. Further, wings 208a and 208b may be in the same plane with respect to each other or may be positioned at an angle with respect to each other. In some embodiments, the angle between the plane of the wings is adjustable. In some embodiments, the elongate assembly is configured such that a treatment assembly, such as a needle assembly, is extendable through the aperture.

In some embodiments, expandable member 200 can be delivered using a sheath. The sheath functions to house expandable member 200 and collapse or compress wings 208a and 208b as the device is delivered to an interventional site of a patient. Once the target site is reached, extension of expandable member 200 through the distal opening of the sheath can be actuated by the handle assembly of the treatment device. As expandable member 200 exits the sheath, wings 208a and 208b expand or spring open, move away from the midline, to contact and manipulate target tissue. This delivery maintains wing alignment while preventing tissue trauma due to the wing edges. According to one embodiment, arms 202a and 202b are fixedly secured to elongate assembly 204 and distal connecting member 206 is free to move longitudinally with respect to wings 208a and 208b to enable expansion and retraction of wings 208a and 208b as they exit the sheath. According to another embodiment, arms 202a and 202b are free to move longitudinally with respect to wings 208a and 208b and distal connecting member 206 is fixedly secured to elongate assembly 204 to enable expansion and retraction of wings 208a and 208b as they exit the sheath.

Figure 10:
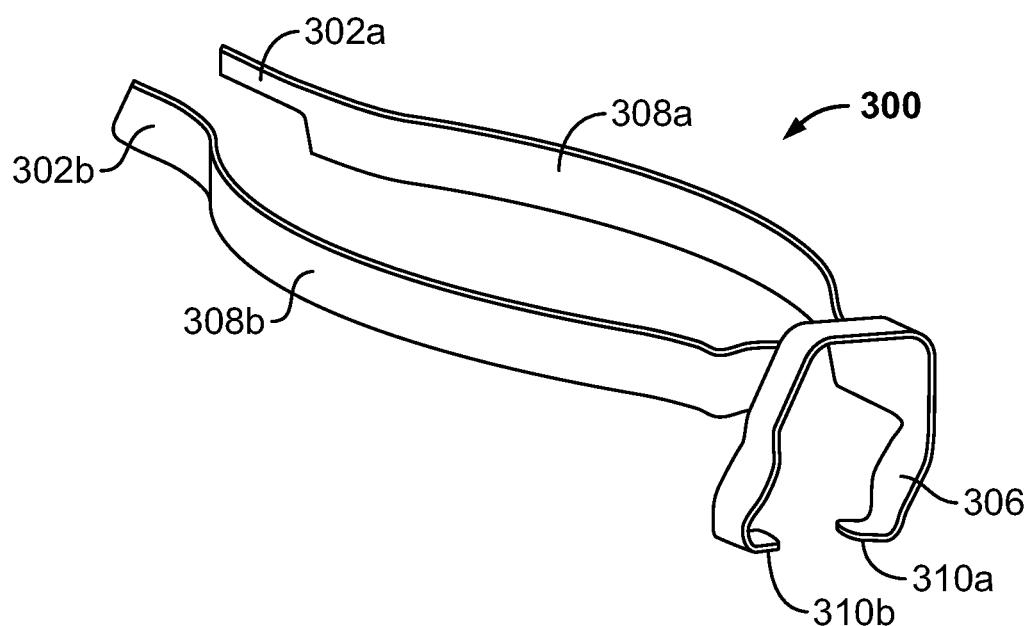
FIG. 10 is a perspective view, depicting another embodiment of an expandable structure that can be employed to engage and manipulate tissue.

FIG. 10 shows another embodiment of an expandable member that can be attached to the distal end of a treatment device. Expandable member 300 can include arms 302a and 302b situated in parallel or substantially in parallel. Each arm can include a portion that is capable of expanding outward past the longitudinal axis of arms 302a and 302b. Wings 308a and 308b can be connected to a distal attachment piece 306 at the distal end of expandable member 300. In one embodiment, distal attachment piece 306 is horseshoe-shaped. Distal attachment piece 306 can be situated in a substantially perpendicular configuration with respect to wings 308a and 308b. Distal attachment piece 306 can include tabs 310a and 310b. Attachment piece 306 can be configured to receive and form a secure connection with a portion of the distal end of a treatment device.

Figure 11:
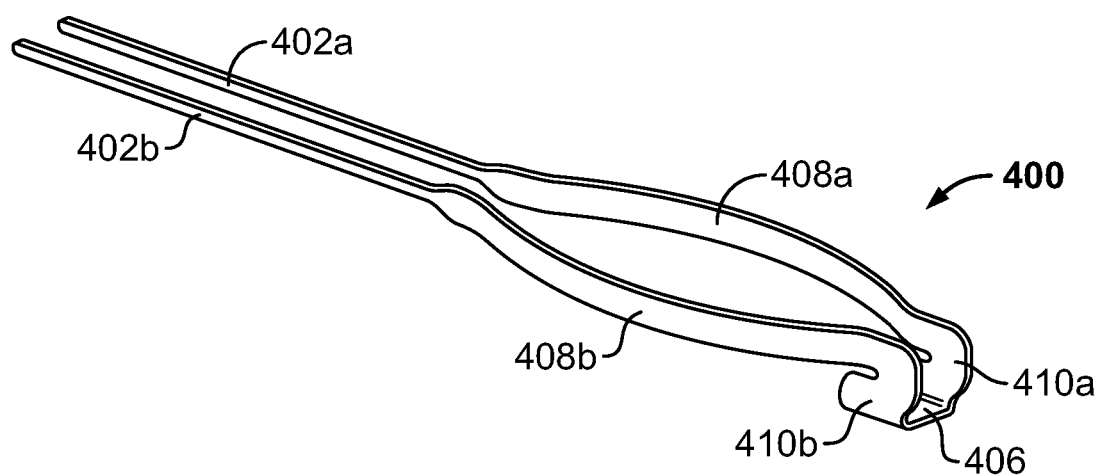
FIG. 11 is a perspective view, depicting another embodiment of an expandable structure that can be employed to engage and manipulate tissue.

FIG. 11 shows another embodiment of an expandable member. Expandable member 400 can include arms 402a and 402b situated in parallel or substantially in parallel. Each arm can include a portion that is capable of expanding outward past the longitudinal axis of arms 402a and 402b. Wings 408a and 408b can terminate with curved ends 410a and 410b, respectively, that connect to create channel 406. Channel 406 can be configured to receive and secure a portion of the distal end of a treatment device.

FIGS. 10 and 11 illustrate configurations of the distal end of the expandable member that facilitate attachment of the expandable member to a treatment device. Other configurations that facilitate attachment of the expandable member to a treatment device are contemplated and the disclosure herein is not limited to the attachment configurations depicted in FIGS. 10 and 11.

Referring again to the embodiment of a treatment device depicted in FIGS. 8A-B, the device is configured such that the needle actuator 108 and the needle retracting lever 110 are in a ready position capable of providing treatment, such as delivery of a tissue anchor. Upon depression of the needle actuator 108, the needle assembly 106 is advanced from within the elongate tissue access assembly 104 (See FIG. 8B). The needle assembly can be configured so that it curves back toward the handle as it is ejected. In use in a prostate intervention, the needle assembly is advanced through and beyond a prostate gland. Spring deployment helps to ensure the needle passes swiftly through the tough outer capsule of the prostate without "tenting" the capsule or failing to pierce the capsule.

After depression of the needle actuator 108 and the unlocking of the needle retraction lever 110, the needle retraction lever 110 can be actuated. Such action results in a withdrawal of the needle assembly 106. In some embodiments, the needle assembly 106 is withdrawn further than its original position within the device pre-deployment. In a prostatic interventional procedure, this action can be used to deliver an implant or various activatable members, such as a tissue anchor, to facilitate modification of prostatic tissue.

The expandable member can be used to position elongate tissue access assembly 104 such that it engages the median lobe prior to and during deployment of an implant and/or modification of prostatic tissue by increasing the surface area of the distal end of assembly 104. The expandable member can also be used to displace and widen the urethral wall.

Figure 12A:
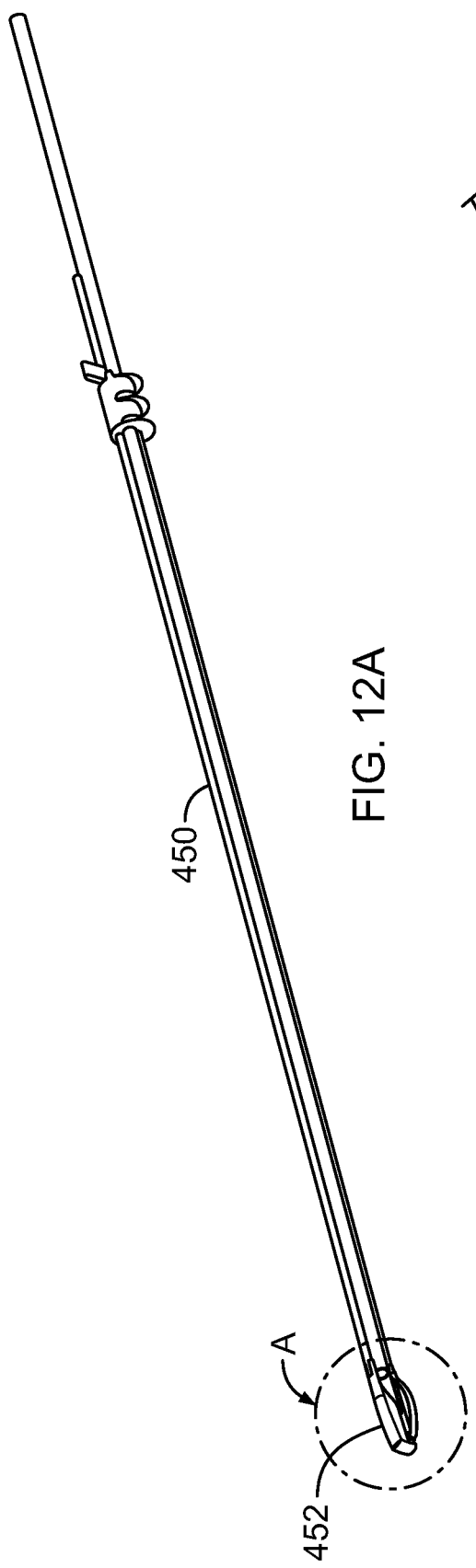
FIG. 12A is a top perspective view, depicting an embodiment of an expandable engagement and manipulation device.
Figure 12B:
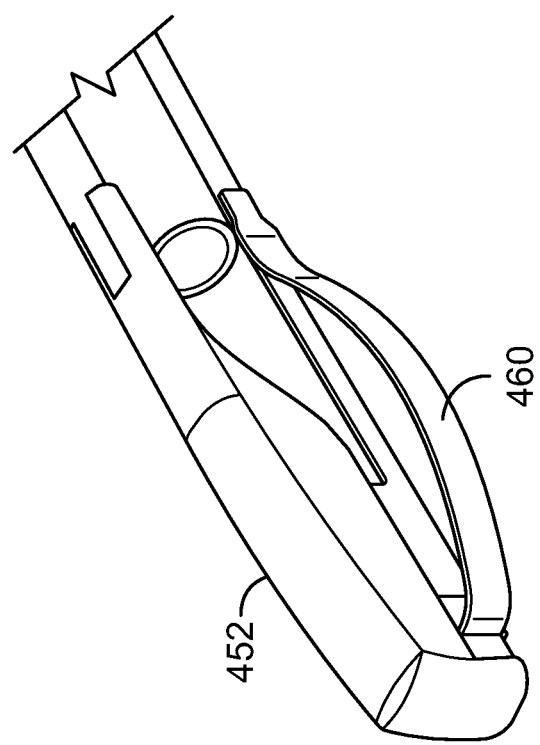
FIG. 12B is an enlarged top perspective view, depicting a distal end portion of an expandable engagement and manipulation device.
Figure 12C:
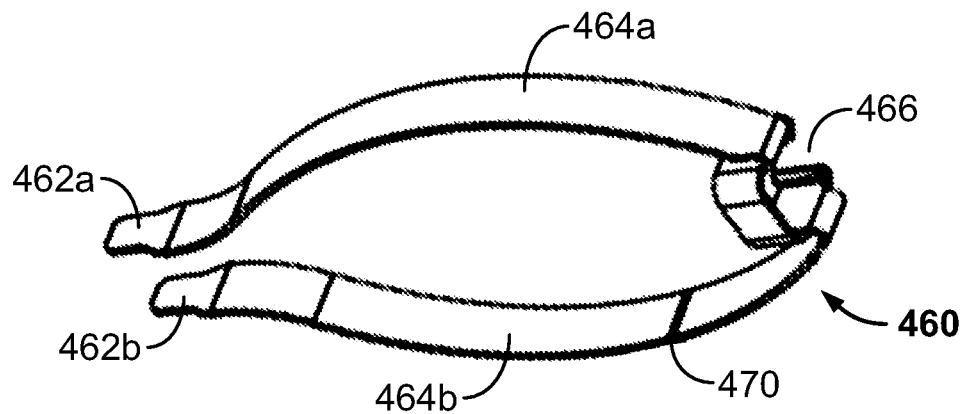
FIG. 12C is a perspective view, depicting another embodiment of an expandable structure that can be employed to engage and manipulate tissue.
Figure 12D:
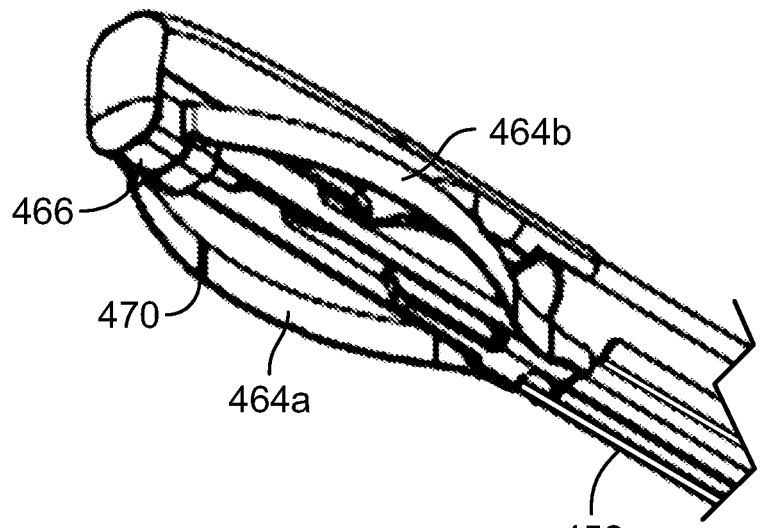
FIG. 12D is an enlarged bottom perspective view, depicting a distal end portion of an embodiment of an expandable engagement and manipulation device.
Figure 12E:
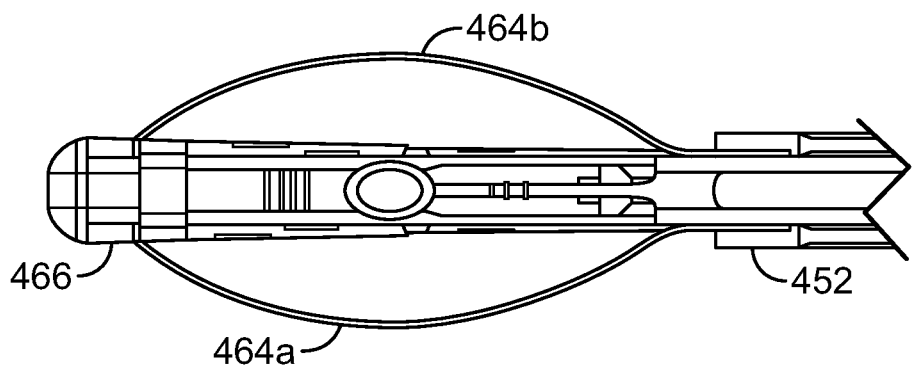
FIG. 12E is an enlarged bottom view, depicting a distal end portion of an embodiment of an expandable engagement and manipulation device.
Figure 12F:
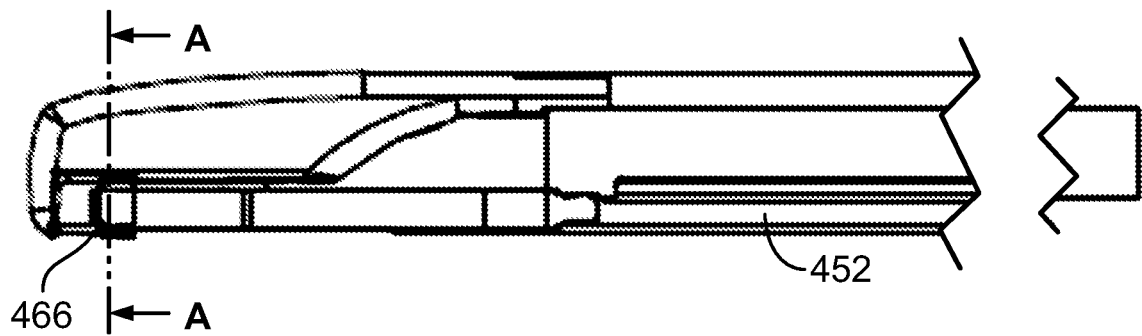
FIG. 12F is an enlarged side view, depicting a distal end portion of an expandable engagement and manipulation device.
Figure 12G:
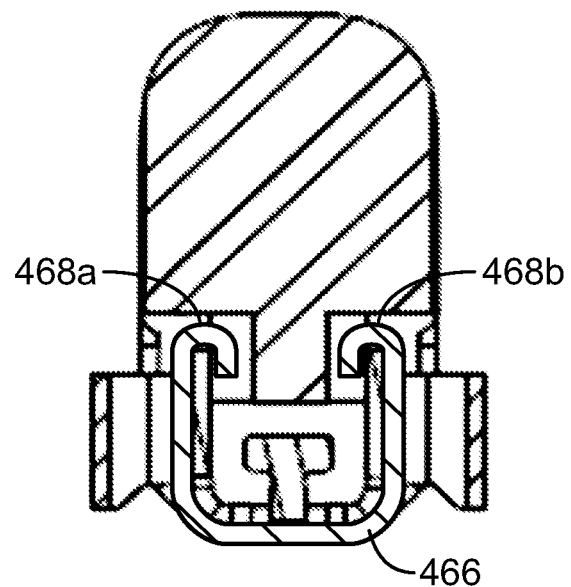
FIG. 12G is a cross-sectional view, depicting a distal end portion of an embodiment of an expandable engagement and manipulation device.

As shown in FIGS. 12A-G, an elongate assembly 450 can include a distal end 452 with an expandable member 460. Expandable member 460 can include arms 462a and 462b situated in parallel and secured to the shaft of distal end 452. Each arm can include an expandable portion, wings 464a and 464b, that expand outward past the longitudinal axis of arms 462a and 462b. The distal end of expandable member 400 can include channel 466 to receive and secure a portion of the distal end of elongate assembly 450. FIGS. 12F & 12G illustrate a cross-section of channel 466 with tabs 468a and 468b that fasten over a portion of the distal end 452 of elongate assembly 450. Insertion of the elongate assembly 450 into channel 466 allows the distal end of expandable member 460 to slide along the shaft of the assembly and facilitate wing position from a "closed" (compressed toward the midline) to an "open" (displaced away from the midline) configuration. Additionally, movement of expandable member 460 relative to the treatment device is constrained to the longitudinal axis of the treatment device. Furthermore, such an alignment presents no additional obstruction to cystoscope or endoscope view when such viewing devices are used during a procedure.

When elongate assembly 450 is inserted into a sheath (not shown), such as when the device is delivered to an interventional site of a patient, wings 464a and 464b reduce in profile by collapsing toward the midline of the longitudinal axis of the distal end the treatment device. Once the target site is reached, wings 464a and 464b can expand away from the midline of the treatment device when the elongate assembly 450 is extended through the distal opening of the sheath. Wings 464a and 464b are then available to engage and manipulate tissue.

In some embodiments, expandable member 460 is made from stainless steel having a 0.006-inch (0.015 cm) thickness. It can be advantageous for the cross-section of the arms and or wings of the expandable member to be asymmetrical. For example, the cross-section can be rectangular or elliptical such that one axis is substantially longer then its orthogonal axis. The purpose of this asymmetry is to provide flexibility in one direction and stiffness in the orthogonal direction. The stiffness facilitates capture and manipulation of tissue, while flexibility facilitates expansion and retraction of the expandable member. In some or the same embodiments, the arms and/or wings are configured with rounded edges to minimize tissue trauma during use. In some embodiments, the internal face of wings 464a and 464b can include visual line marker(s) 470 that indicate an entry position for a needle assembly (not shown) that exits from the side of elongate assembly 450.

Other embodiments of structures that can be used to better engage and manipulate target tissue, including the median lobe of the prostate, are contemplated below. In some embodiments, wings 508a and 508b can be deployed from an expandable member 500 using a pair of telescopic arms. As shown in FIGS. 13A-13D, wing 508a is attached to or continuous with arm 502b. Arms 502a and 502b can be coupled within sleeve 522a such that arm 502b glides along stationary arm 502a (indicated by the dashed arrow in FIG. 13C) to transition from a contracted to an expanded state while simultaneously transitioning wing 508a outward from the longitudinal axis of member 500 from a compressed ("closed") to an expanded ("open") state. Expandable member 500 can be inserted into a sheath for placement at an interventional site. Once the device is positioned at the target site, the delivery device can be actuated to deploy arms 502b and 502d from sleeves 522a and 522b, respectively, to engage target tissue.

Figure 14A:
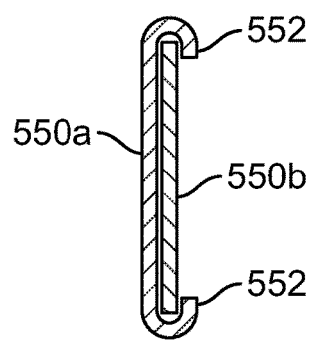
FIGS. 14A-B are cross-sectional views, depicting alternative configurations for telescoping arms.
Figure 14B:
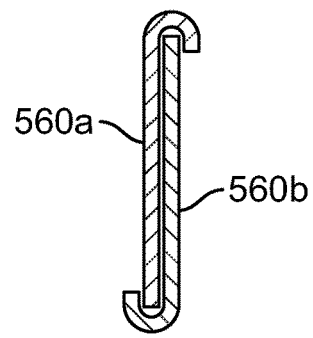

Alternative embodiments of telescopic arms are illustrated in FIGS. 14A & 14B. In FIG. 14A, interlocking arms 550a and 550b are shown. Arm 550a can house arm 550b and include rounded ends 552 that cover the top and bottom edges of arm 550b. In FIG. 14B, each of interlocking arms 560a and 560b have a rounded end and a flat end. When interlocked, the rounded end of each arm covers the flat end of the opposite arm.

In the telescopic arm design of FIGS. 13A-13D and FIGS. 14A & 14B, the stationary arms can be secured to the shaft of the elongate assembly of the delivery device. Such a design provides guided, stabilized alignment and delivery of wings, or a similarly looped distal end, to an interventional site.

Figure 13A:
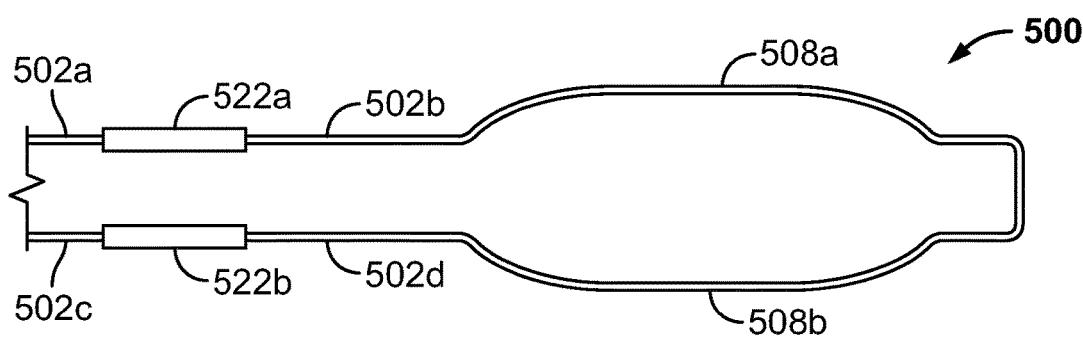
FIG. 13A is a top view, depicting an embodiment of an expandable structure with telescoping arms that can be employed to engage and manipulate tissue.
Figure 13B:
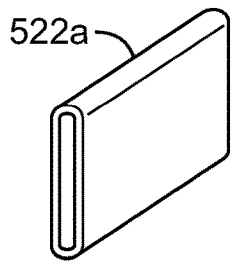
FIGS. 13B-D are various partial perspective views, depicting telescoping arms of an expandable structure that can be employed to engage and manipulate tissue.
Figure 13C:
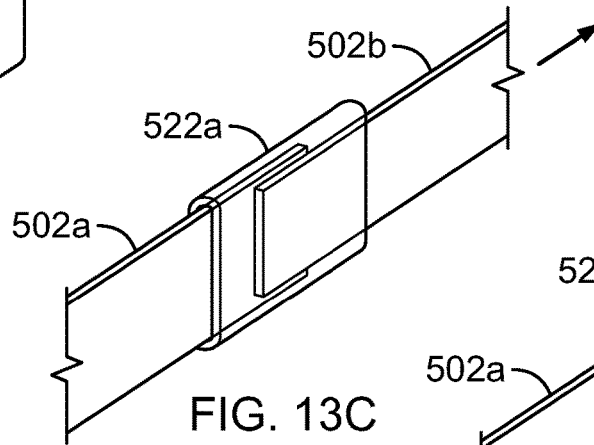
Figure 13D:
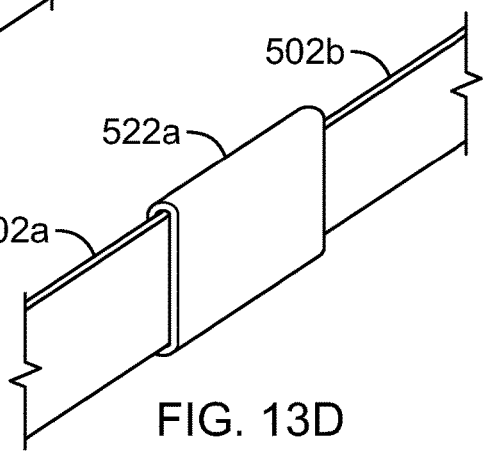

Turning now to FIGS. 15A-D, an approach to engaging and manipulating an enlarged median lobe ML is presented. Such an approach can be used as a complementary therapy with treatments for lateral lobes or can be employed solely to treat a median lobe ML. Because an enlarged median lobe ML can extend into the urinary bladder UB and may act as a ball valve interfering with normal function (See FIGS. 15A and 15B; FIG. 13B is a view through the prostatic urethra and into the urinary bladder), moving tissue away from a ball valve location (that is, away from the bladder neck) may be desired. By avoiding such invasive approaches (such as TURP), there is significantly less risk of disrupting the nerve tissue and/or the smooth muscle of the bladder neck. With less disruption to these tissues, ejaculating function and continence complications will likely be lower.

Accordingly, an approach involving inserting a device into the prostatic urethra UT transurethrally to compress and/or displace the median lobe ML is contemplated. Once the lobe is compressed or displaced, other procedures such as implanting tissue anchors or implants in a specific direction to maintain the compression/displacement of the median lobe.

Figure 15A:
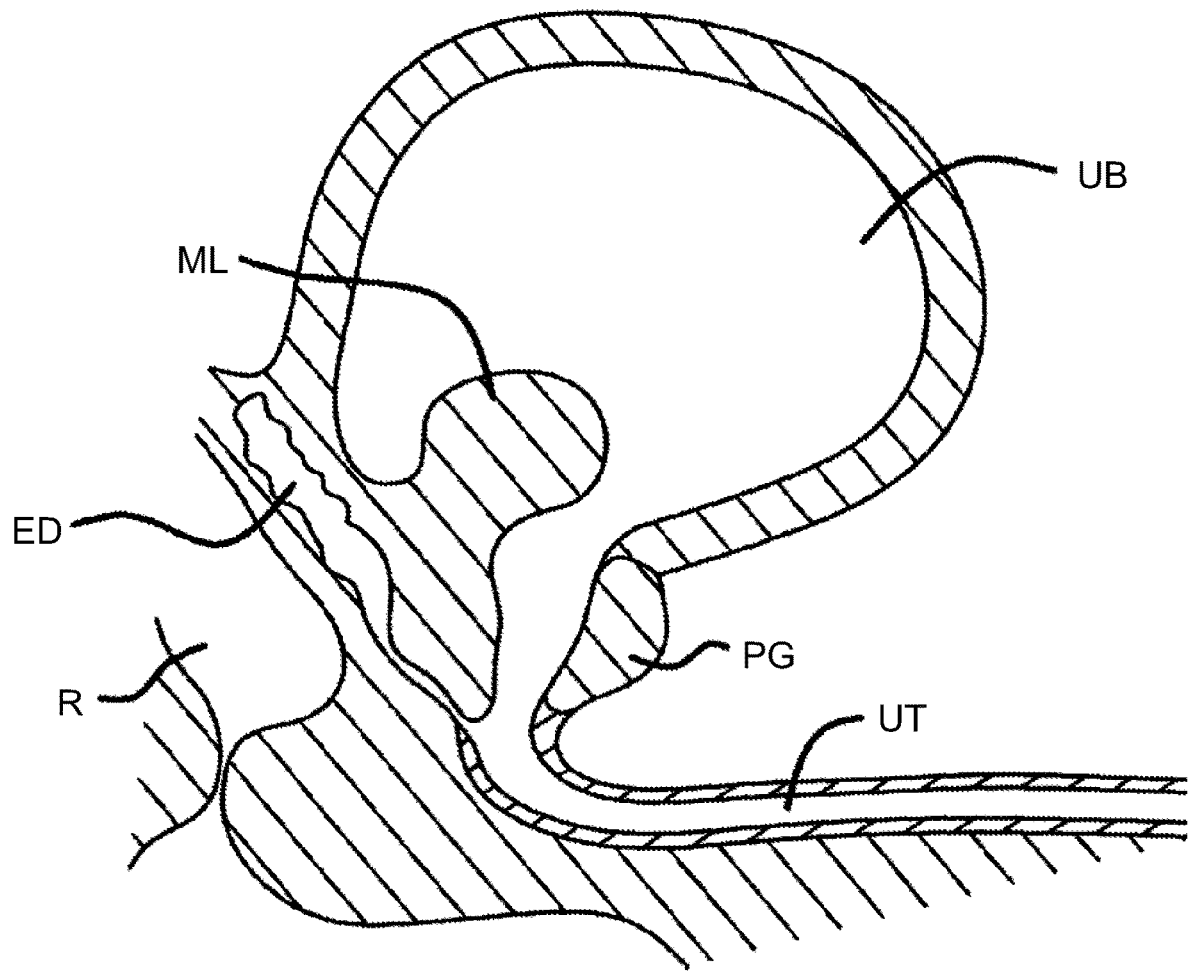
FIGS. 15A-D are various cross-sectional views, depicting details of an approach to engaging, compressing and manipulating a median prostate lobe of a prostate.
Figure 15B:
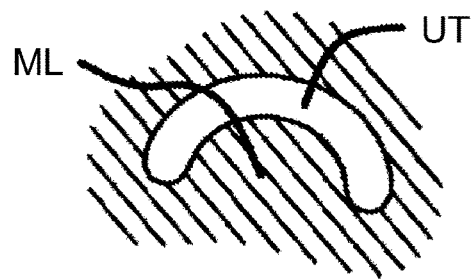
Figure 15C:
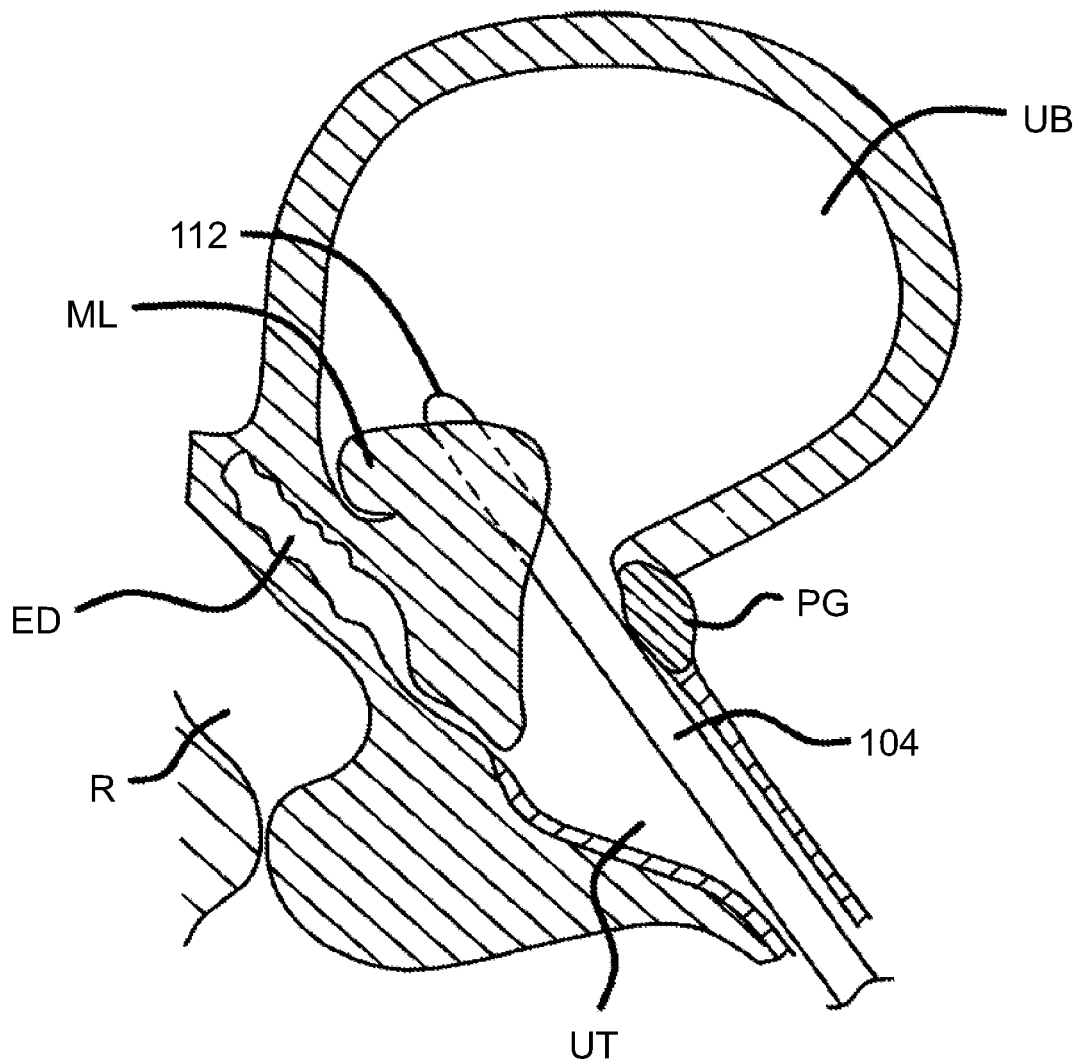
Figure 15D:
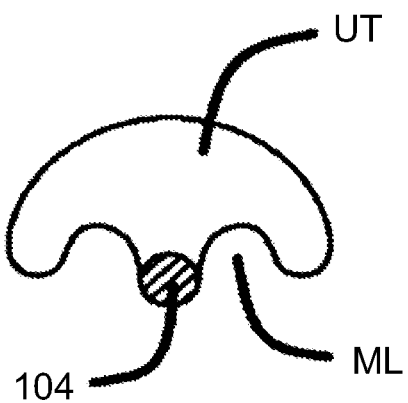

As an initial step, sagittal views of a patient's bladder and prostate can be taken using transabdominal or transrectal ultrasonography. In this way, the patient's anatomy can be assessed. In this regard, an intravesical prostate measurement is taken to determine the vertical distance from a tip of the median lobe protrusion to the base of the bladder. As shown in FIGS. 15C-D, after assessing the anatomy, the elongate tissue access assembly 104 of an anchor delivery device (See FIGS. 8A and 8B) is advanced within the urethra UT and into apposition with the median lobe ML. FIG. 15D is a view through the urethra UT depicting the compression and displacement of the median lobe ML.

One specific series of actions is to position the tissue access assembly 104 so that its terminal end 112 is anterior to a prominent portion of the median lobe ML and then displace the surface in the posterior direction to move the median lobe ML away from a centerline of the urethra lumen UT. The median lobe consequently forms a tissue fold (See FIG. 15D) about the delivery instrument. In embodiments in which an expandable member is used to engage and manipulate the median lobe, the expandable member provides increased surface area as compared to tissue access assembly 104 in FIG. 15D, which facilitates temporary capture of the median lobe so that it can be displaced. In some embodiments, tissue of the median lobe can be captured in the space between the wings of the expandable member and the distal end of the elongate tissue treatment device. Thus, the wings of the expandable member can be configured to promote such capture, including by varying the amount of expansion that the wings undergo during deployment and retraction.

Figure 16A:
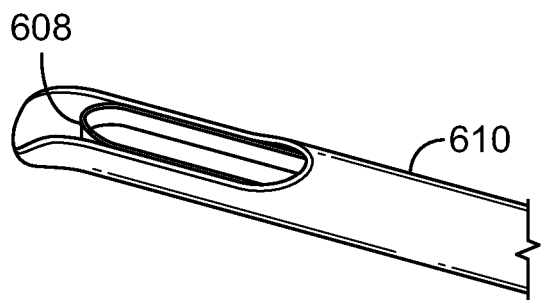
FIG. 16A is a perspective view, depicting a distal end portion of an expandable structure that can be employed to engage and manipulate tissue housed in a sheath.
Figure 16B:
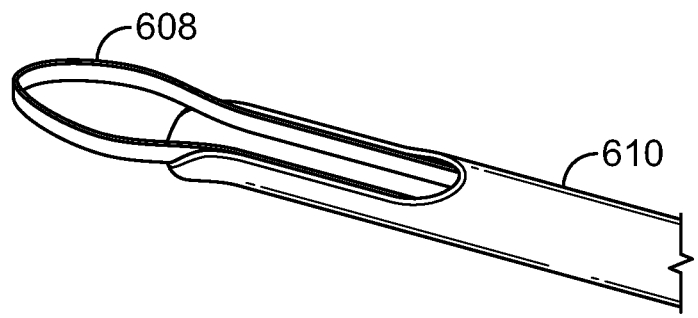
FIG. 16B is a perspective view, depicting the distal end portion of the expandable structure of FIG. 16A in an expanded state after exiting the sheath.

FIGS. 16A & 16B illustrate another embodiment of a looped or expandable member. In this embodiment, a looped member 608 can be housed in the distal end of a sheath 610 such that the expandable wing portion of looped member 608 is compressed. When an elongate assembly is passed through sheath 610, it contacts the proximal end of looped member 608 (not shown) and pushes the wing portion out of sheath 610, allowing it to expand and manipulate target tissue.

Figure 17A:
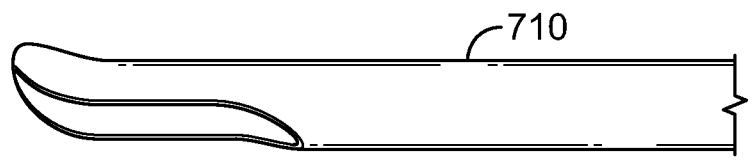
FIG. 17A is a perspective view, depicting the distal end of a sheath.
Figure 17B:
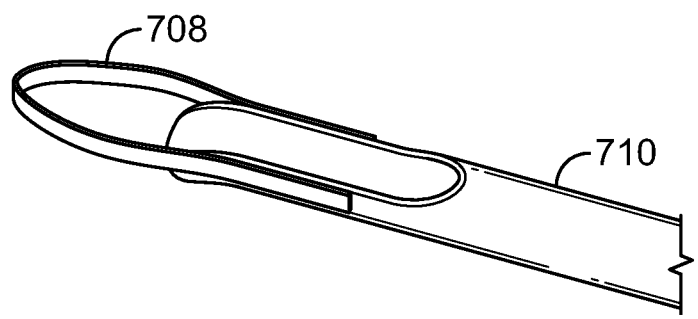
FIG. 17B is a perspective view, depicting an expanded structure that can be employed to engage and manipulate tissue attached to a sheath.

In some embodiments, a looped member 708 can be attached to the distal end of a sheath 710, as shown in FIGS. 17A & 17B. In these embodiments, looped member 708 can expand and/or manipulate tissue at an interventional site prior to deployment of an elongate assembly. In some embodiments, looped member 708 can be made of a level ribbon, that is, having a linear cross-section. In other embodiments, looped member 708 can be made of a semi-circular ribbon having a c-shaped cross-section to prevent the edges of the device from contacting patient tissue during delivery.

Figure 18A:
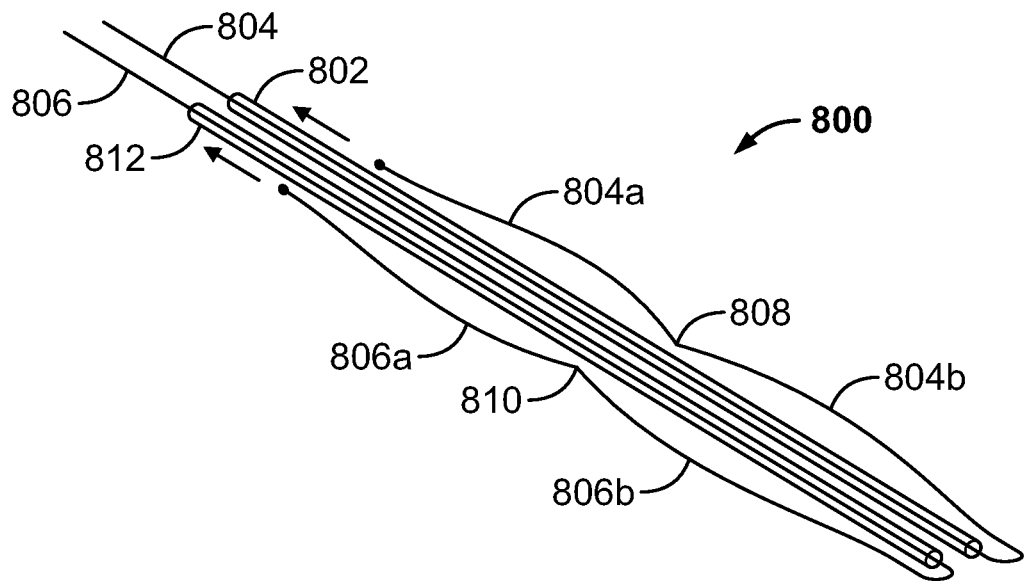
FIG. 18A is a perspective view, depicting an embodiment of an expandable wire structure that can be employed to engage and manipulate tissue, in a contracted state.
Figure 18B:
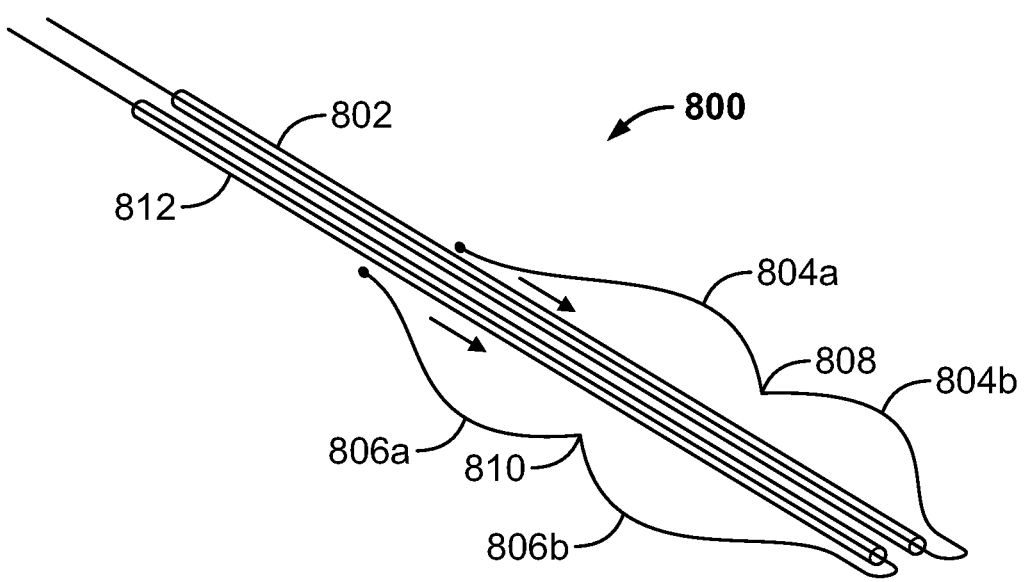
FIG. 18B is a perspective view, depicting an embodiment of an expandable wire structure that can be employed to engage and manipulate tissue, in an expanded state.
Figure 19A:
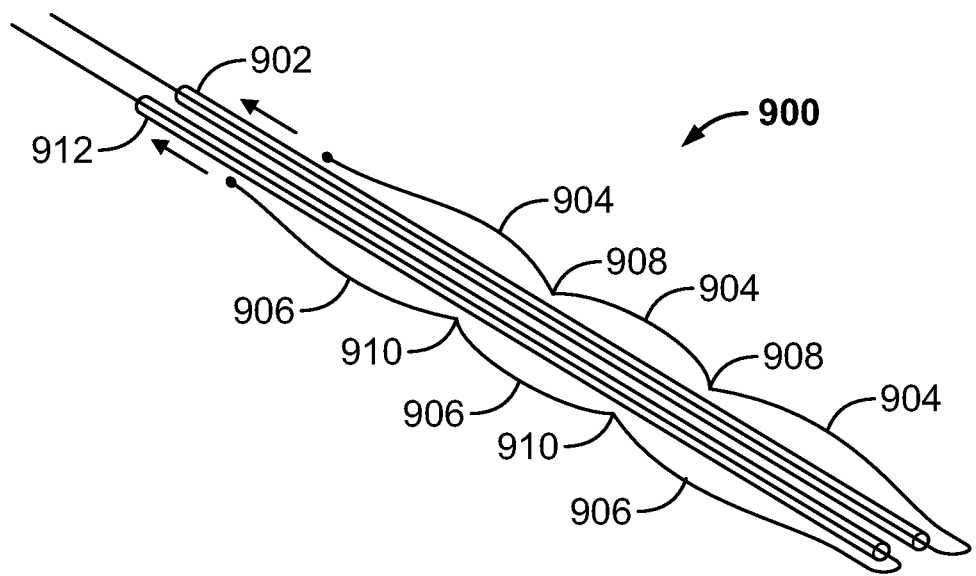
FIG. 19A is a perspective view, depicting another embodiment of an expandable wire structure that can be employed to engage and manipulate tissue, in a contracted state.
Figure 19B:
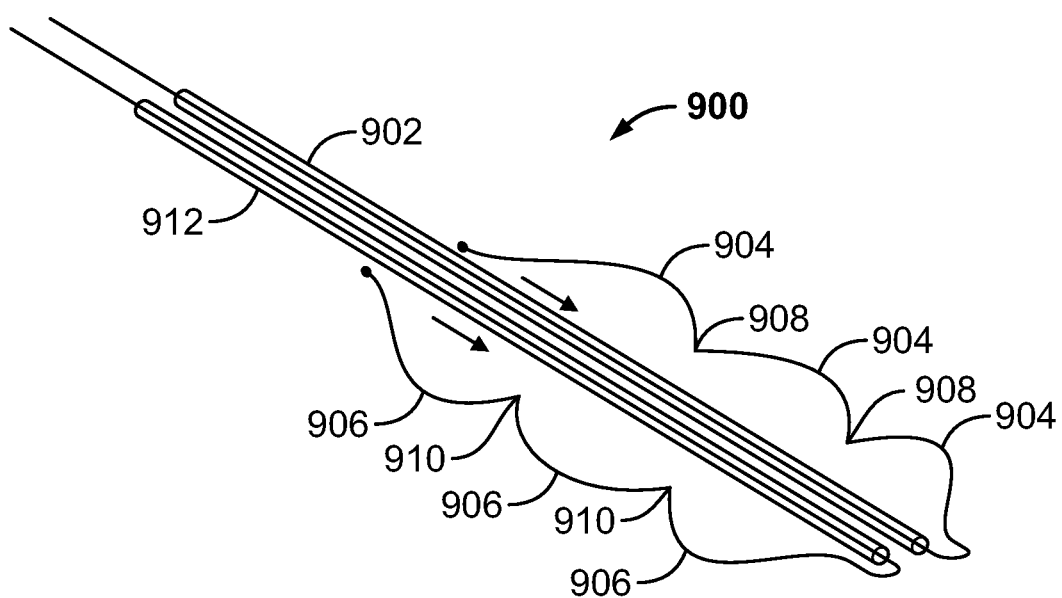
FIG. 19B is a perspective view, depicting another embodiment of an expandable wire structure that can be employed to engage and manipulate tissue, in an expanded state.

Alternative embodiments of an expandable member are shown in FIGS. 18A & 18B and 19A & 19B. Expandable member 800 can include a pair of tubes 802 and 812 attached to opposite sides of the shaft of an elongate assembly of a delivery device (not shown). Such tubes can be biased to the distal end of the elongate assembly. Tubes 802 and 812 can house wires 804 and 806, respectively, which are threaded through the lumen of the tube and then exit the distal end of each tube. The wire that exists the tube is positioned substantially parallel to the outer length of each tube and is bent, bowed, arced, or otherwise curved. As shown in FIGS. 18A & 16B, wire 804 includes a pair of expandable portions 804a and 804b with a cinched waist 808 therebetween and wire 806 includes a pair of expandable portions 806a and 806b with a cinched waist 810 therebetween. In some embodiments, the cinched waist of each wire can be a compression spring coil that allows the expandable portions to collapse toward or expand from the midline of the elongate assembly. FIG. 18A illustrates expandable member 800 in a compressed or collapsed state, such as when the elongate assembly is housed within a sheath (not shown). FIG. 18B illustrates expandable member 800 in an expanded state, such as when the elongate assembly exits the distal end of a sheath (not shown) freeing the springs to lengthen and, in turn, move the expandable portion of each wire away from the midline of the treatment device. FIGS. 19A and 19B illustrate another embodiment of expandable wire structures that function similar to expandable member 800, but expandable member 900 includes three expandable portions.

Figure 20A:
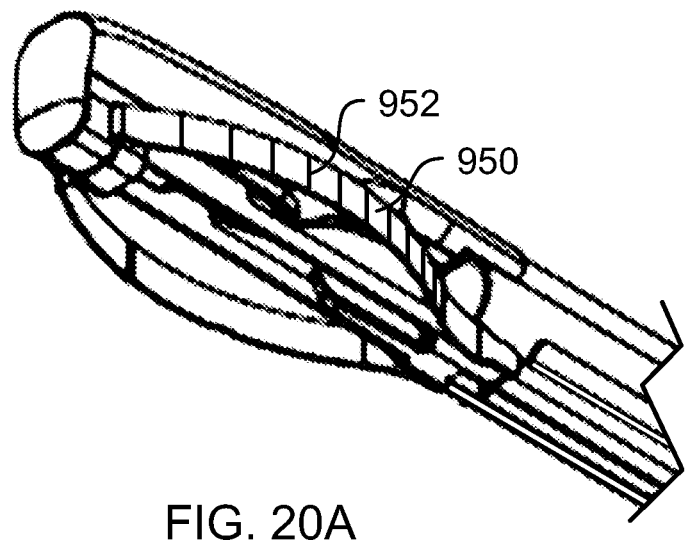
FIGS. 20A-C are enlarged perspective views, depicting a distal end portion of an expandable engagement and manipulation device incorporating various supplemental tissue engagement structures.
Figure 20B:
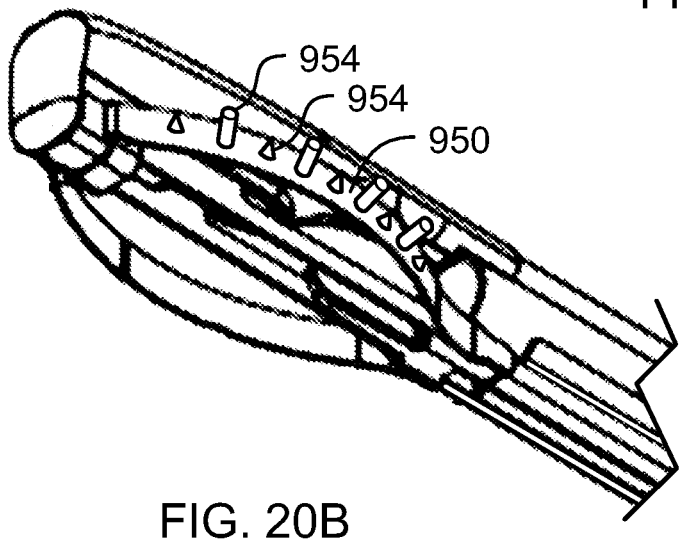

Various approaches are contemplated for best engaging median lobe or other tissue. Additional structural features can be incorporated into the distal end of the expandable member of treatment device 100 for the purpose of increasing frictional forces between the target tissue and a distal portion of the treatment device 100, or for increasing the surface area of the treatment device. Knurled or roughened surfaces 952 can form surface components of portions or an entirety of the winged or expandable portions 950 (See FIG. 20A) of the treatment device 100. In some embodiments, as shown in FIG. 20B one or more of spikes, fangs, hooks, barbs or other protuberances 954, or a combination thereof can be configured to extend at various angles and lengths from expandable portion 950. Such protuberances can be sharp or blunted. Such structures can be one or more of retractable, flexible or fixed. Thus, in one or more approaches, these structures can be associated with a pop-up feature attached to a puller (not shown). In one aspect, control of the of the pop-up feature can be achieved with side actuators to deploy and retract extendable tissue engaging and manipulation features when slid down the sheath and a spacer to change a relationship between the sheath and shaft for controlling deployment of the side actuators. In one particular approach, the spikes, fangs, hooks, barbs, or protuberances can be angled proximally so that enhanced tissue engagement is provided when withdrawing the delivery device and is released when advancing the delivery device.

Atraumatic tape can be placed over the spikes, fangs, hooks, barbs, or protuberances 954 prior to use of the treatment device 100. The tape can be removed prior to performing a median or middle lobe procedure. It is thus contemplated that the treatment system can be provided in two configurations. A first configuration can be for normal use such that it includes atraumatic tape that covers sharp or other tissue engaging features and prevents them from interacting with the tissue. A second configuration can be for median lobe engagement and manipulation usage, where the system is assembled and shipped without atraumatic tape covering sharp or other tissue engaging features.

Figure 20C:
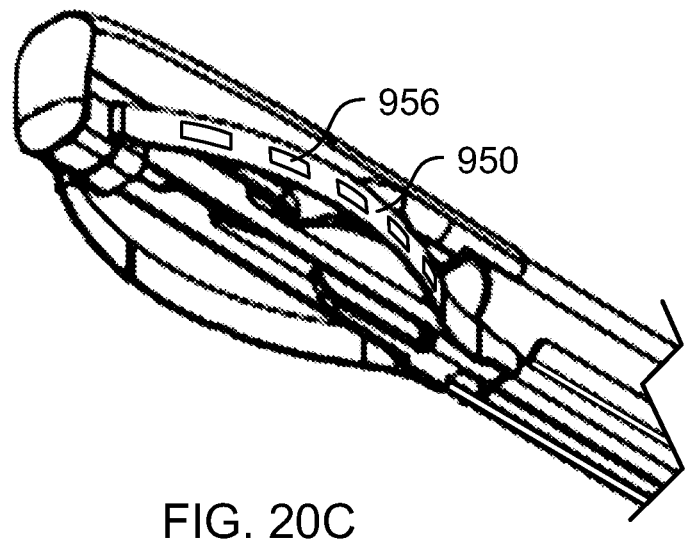

In some embodiments, tissue adhesive material 956 can be added to the exterior surface at various locations along expandable portion 950 (See FIG. 20C). In certain contemplated approaches, such tissue adhesive material 956 can range from adhesive tape to material that is swellable in fluid such that it changes its adhesion property when desired. Another contemplated approach to adhesion upon pressure involves scale-like projections 958 (FIGS. 20F & 20G) incorporated onto expandable portion 950. High friction is created when pulling the target tissue in a direction against the scales, but no or little or less friction after deployment or when employing the treatment device 100 with the direction of scales 958. Here also, such structure can be one or more of retractable, flexible or fixed.

Structures that provide enhanced frictional or other engagement forces also can be based upon an adhesive that responds to pressure. For example, the expandable distal portion of treatment device 100 can additionally or alternatively include micro-hooks similar to Velcro technology, the same requiring tissue to be pressed against it to create a secure engagement.

As stated, such tissue engaging structures can be placed in various locations along the expandable portion of treatment device 100. Textures or protuberances can be configured to engage tissue such that tissue will roll with the distal end of the device as it is rotated, for example, into a deployment position. In some embodiments, the structures can be located on side areas of the treatment device where there is more space. That is, these structures can be located away from the exit points for the therapeutic elements that may extend from the treatment device. It is specifically contemplated that structures can be located along a "tissue contacting fence." That is, protuberances can be hidden from tissue contact in a "tissue contacting fence" and configured to extend beyond this protective fence via a user operated actuator.

Figure 20D:
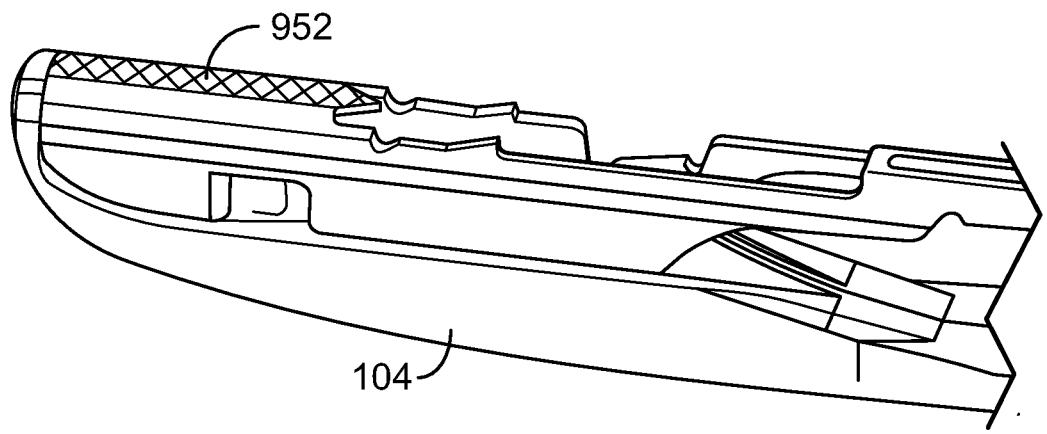
FIGS. 20D-F are enlarged perspective views, depicting a distal end portion of a tissue access and a device incorporating various supplemental tissue engagement structures.
Figure 20E:
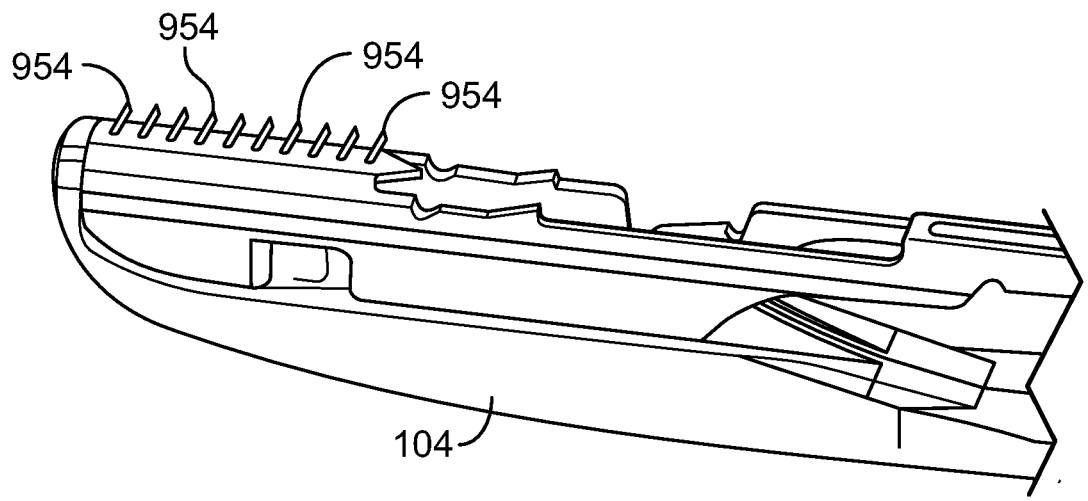
Figure 20F:
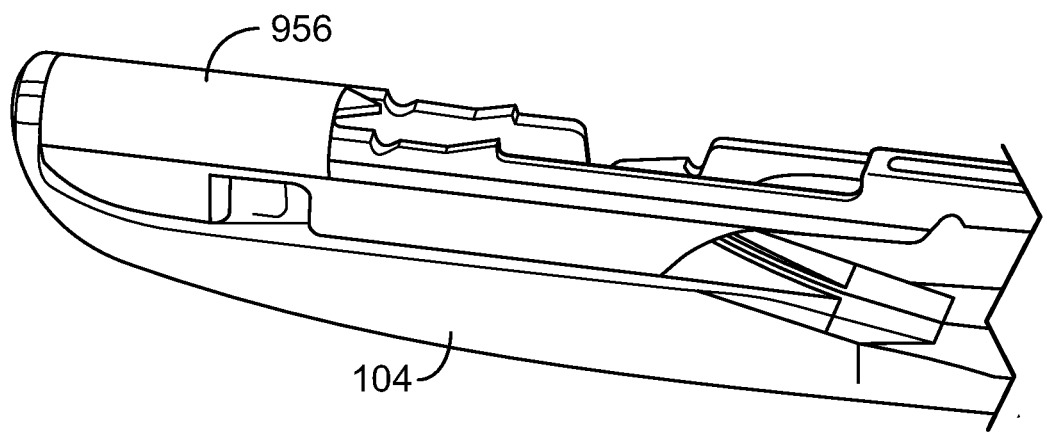
Figure 20G:
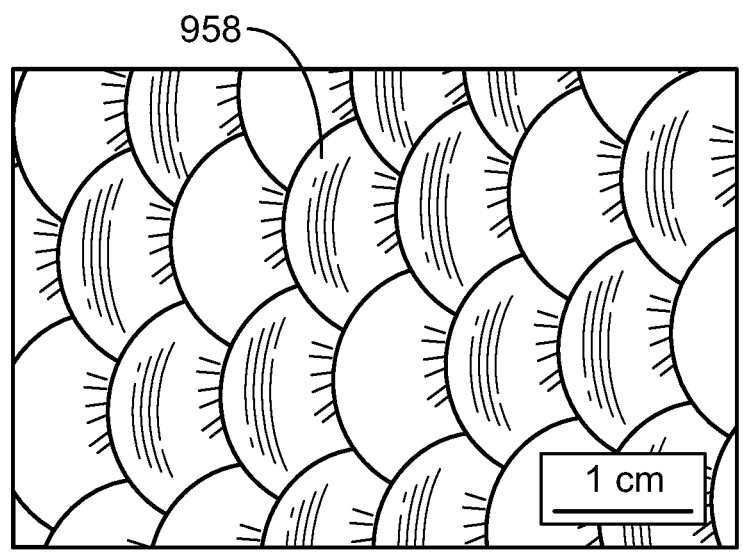
FIGS. 20G-H are enlarged views, depicting structures that can be incorporated into the distal end portion of a tissue engagement and manipulation device.
Figure 20H:
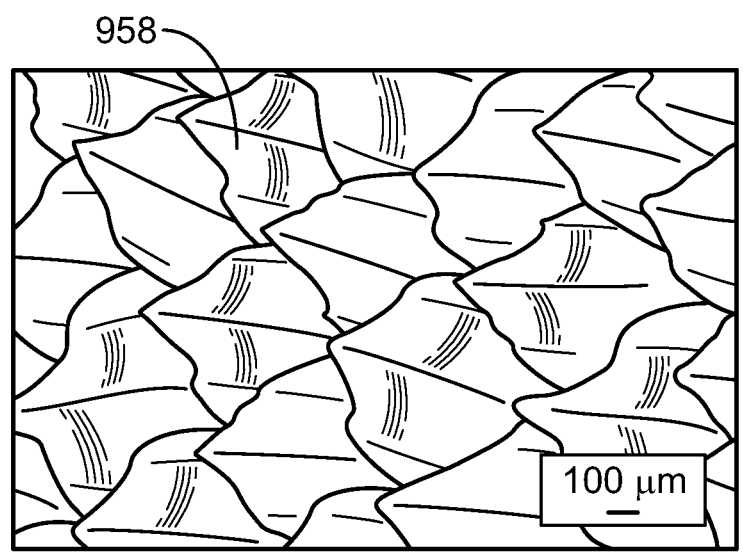

Referring now to FIG. 20D-F, elongate tissue access assembly 104, and in particular the distal end of elongate tissue access assembly 104, can include knurled or roughened surfaces 952, spikes, fangs, hooks, barbs, or protuberances 954 (and, optionally, atraumatic tape), and/or tissue adhesive material 956. In certain embodiments, one or both of the elongate tissue access assembly and the expandable member can contain one or more of these features. That is, the embodiments described above, illustrated in FIGS. 20A-H, can be incorporated into treatment device 100 to supplement, or enhance, the tissue engagement and manipulation capacity of the expandable or winged portion of the device, of the distal end of the elongate tissue access assembly, or both.

Vacuum forces can also be employed to facilitate engaging and manipulating tissue. In this regard, a suction or vacuum source (not shown) can be incorporated into the expandable portion or attached thereto, and a channel provided to communicate with the distal end of the treatment device 100. In this way, the vacuum forces can be initiated and controlled when the treatment device 100 is positioned to engage and manipulate target tissue.

Figure 21:
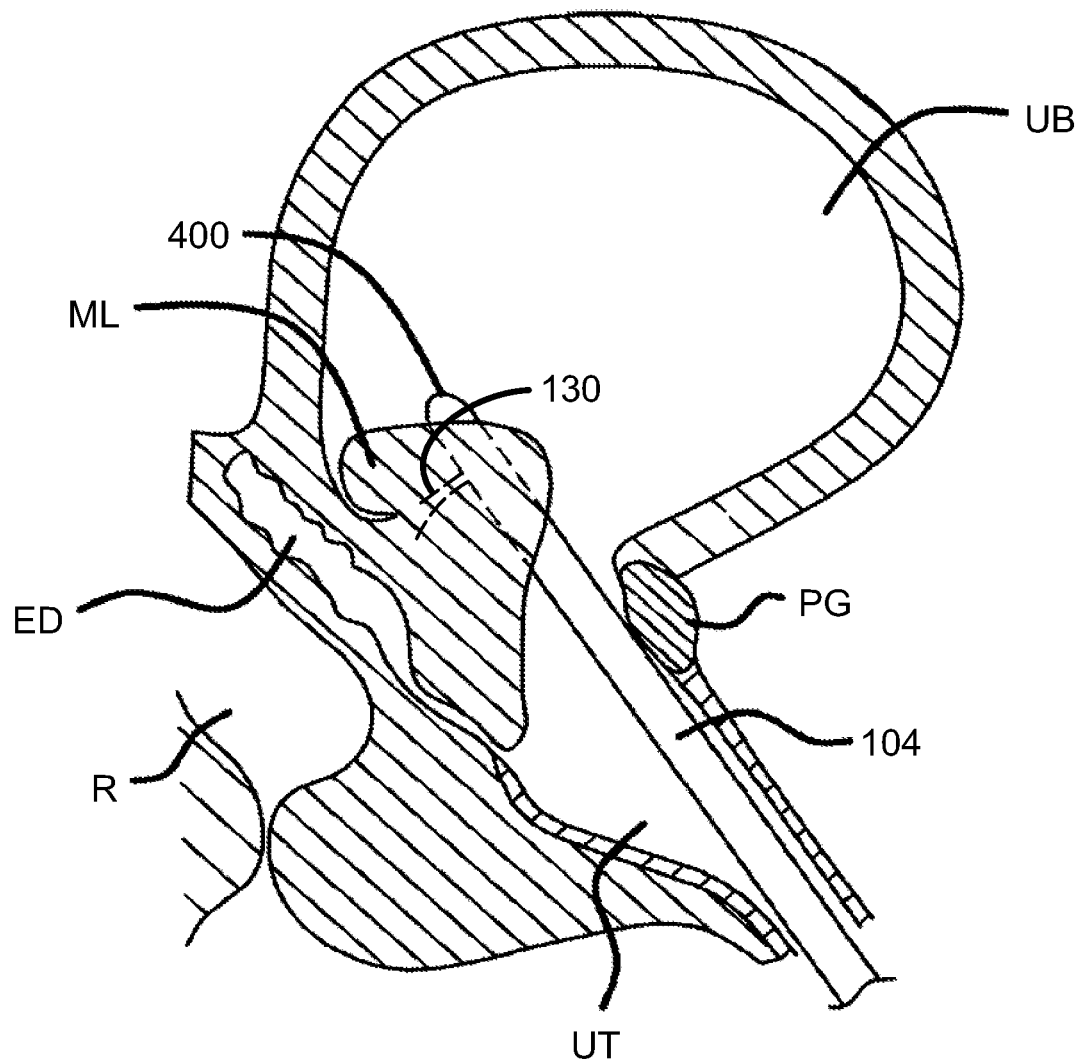
FIG. 21 is a partial cross-sectional view, depicting yet another approach to engaging and manipulating target tissue.

As shown in FIG. 21, in another approach, partial controlled deployment of the needle 230 can be utilized to engage and manipulate target tissue. The needle 230 can be retracted for later full deployment associated with, for example, implantation of an anchor device. Additionally or alternatively, one or more supplemental, side-projecting needles 609 (shown in dashed lines in FIG. 22) can be provided for engaging and manipulating purposes. Various approaches to reinforcing the distal portion of the needle 230 also contemplated so that a more robust structure is presented for tissue manipulation. For example, a supplemental needle tip 610 can be attached to a terminal and portion of the needle 230. In one contemplated approach, the needle tip 610 can be attached to structure that is configured to be actuated from the delivery device handle. The needle 610 can define a solid member to thereby provide sufficient mechanical strength for manipulating tissue, and be connected to any elongated member that extends within the delivery device which extends along and outside of the delivery device but within an introducer sheath or through fluid holes therein. Manual or automated approaches to control the use or removal of the needle tip 610 are both envisioned.

Figure 22:
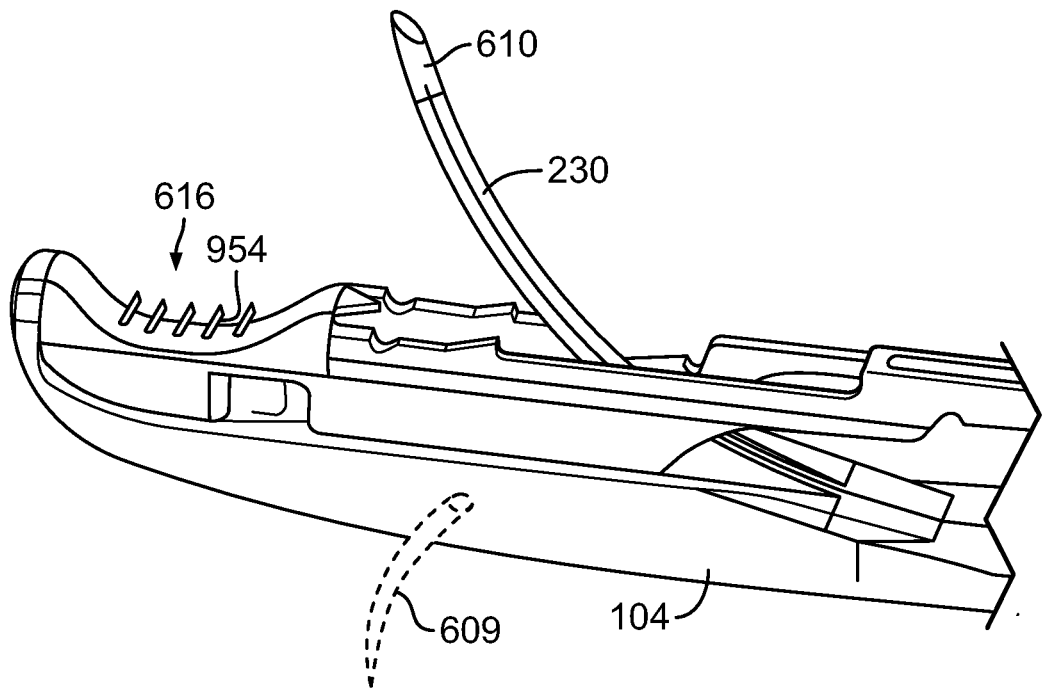
FIG. 22 is an enlarged view, depicting further structure incorporated into an engagement and manipulation device.
Figure 23:
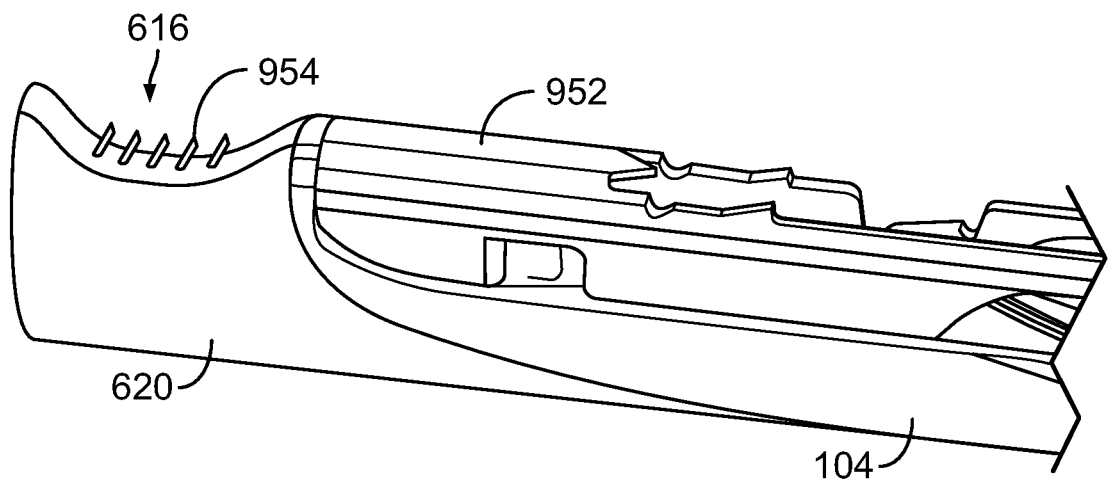
FIG. 23 is an enlarged view, depicting supplemental structure forming part of an engagement and manipulation device.

With reference to FIG. 22, the distal end portion 104 of the delivery device 100 can also, additionally or alternatively, include a divot or recess having a radius of curvature that matches, or generally receives, the contours of the median lobe or other target tissue. The interior of the recess can be configured with any of the described structures for engaging and manipulating tissue. For example, FIG. 22 illustrates recess 616 as including a plurality of spikes 954. Referring now to FIG. 23, a second or supplementary sheath 620 can be provided and configured about the distal portion 104 of delivery device 100. Sheath 620 itself can include one or more of the tissue engaging and manipulating features described herein. Such features can be reserved for one or more sides or portions of the sheath 620 or can be positioned completely around sheath 620. Additionally, sheath 620 itself can include recess 616 configured to match tissue anatomy. Thus, recess 616 can be included in distal end 104 of delivery device 100 by fabricating distal end 104 with a recess 616, or by using sheath 620 that have been fabricated with a recess 616.

The target tissue or median lobe specifically can be pre-treated to facilitate engagement with the treatment device 100. In this regard, it is contemplated that the target tissue can be subjected to electro-cauterization, botox or other modality to alter its mechanical profile. The target tissue can alternatively or additionally be pre-treated by making incisions therein. Finally, the target tissue can be lassoed to support the tissue or to accomplish the desired manipulations.

It is to be recognized that various materials are within the scope of the present disclosure for manufacturing the disclosed devices. Moreover, one or more components disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the disclosure has been described hereabove with reference to certain examples or embodiments of the disclosure but that various additions, deletions, alterations and modifications may be made to those examples and embodiments without departing from the intended spirit and scope of the disclosure. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Briefly and in general terms, the present disclosure is directed towards an apparatus and method for engaging and manipulating internal body structures. Such engagement and manipulation can form the primary or alternatively, form a supplementary or integral part of a multi-step interventional procedure. In one aspect, the apparatus includes elongate member configured to engage tissue in order to manipulate or reposition that tissue. In some embodiments, the tissue is a prostate. In some embodiments, the tissue is the median lobe of a prostate.

In various approaches, the apparatus can include a portion that is equipped with structure that increases frictional forces between the apparatus and tissue to be manipulated. The apparatus can additionally or alternatively include an extendable needle that can be partially deployed to engage or manipulate target tissue. A retractable sheath can also additionally or alternatively be provided to facilitate engaging and manipulating tissue. Further, the surface area of a distal end portion of the apparatus can include structure(s) intended to increase surface area and thus present structure(s) specifically configured to effectively engage or manipulate tissue. Moreover, the apparatus can be configured and employed to pre-treat target tissue by subjecting the tissue to energy or substances that alter the mechanical profile or by creating incisions therein.

Thus, the delivery apparatus of the present disclosure can additionally include various subassemblies which are mobilized via an actuator or other manually accessible structure. The operation of the subassemblies is coordinated and synchronized to ensure accurate and precise navigation and placement of the tissue engaging or manipulation structure.

Figure 24A:
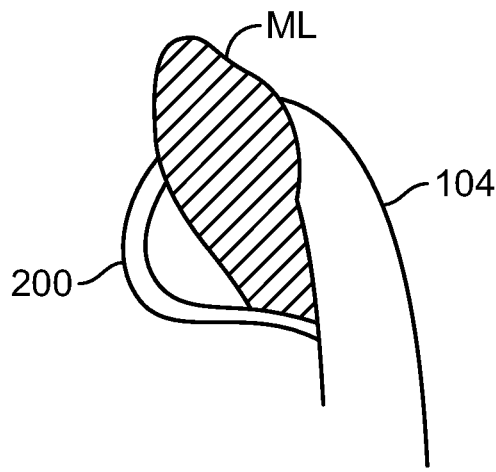
FIGS. 24A-B are enlarged views, depicting structures that can be incorporated into the distal end portion of a tissue engagement and manipulation device and methods for engaging and manipulating tissue.
Figure 24B:
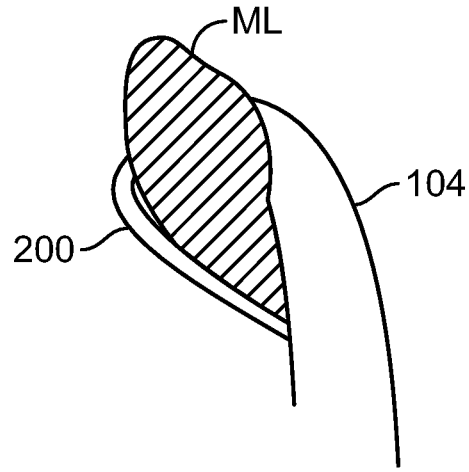

Referring now to FIG. 24A-B, in some embodiments expandable member 200 is adjustable. FIGS. 24A and 24B illustrate a distal end of elongate tissue access assembly 104 and expandable member 200 present on one side of elongate tissue access assembly 104. That is, in this particular embodiment there is only one set of arms or wings. FIG. 24A illustrates expandable member 200 in an expanded state, while FIG. 24B illustrates expandable member 200 in a contracted state. Median lobe ML can be captured within the space between expandable member 200 and elongate tissue access assembly 104. Then, expandable member 200 can be contracted or cinched down such that median lobe ML is secured within the space between expandable member and elongate tissue access assembly 104. In this position, median lobe ML can be manipulated and/or displaced.

Figure 25A:
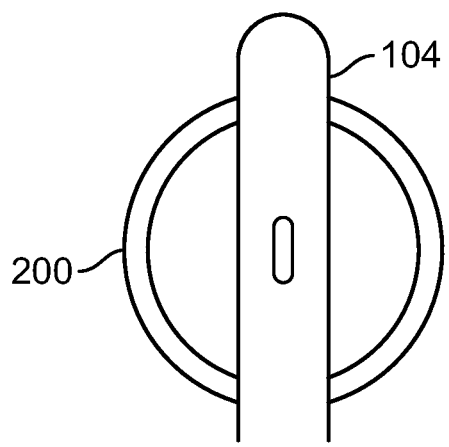
FIGS. 25A-B are enlarged views, depicting structures that can be incorporated into the distal end portion of a tissue engagement and manipulation device.
Figure 25B:
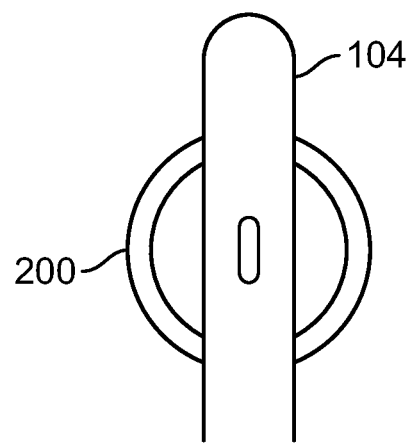
Figure 26A:
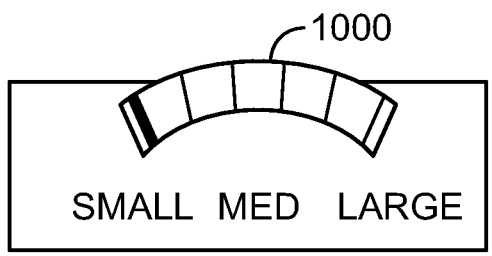
FIGS. 26A-B are enlarged views, depicting structures that can be incorporated into the handle portion of a tissue engagement and manipulation device.
Figure 26B:
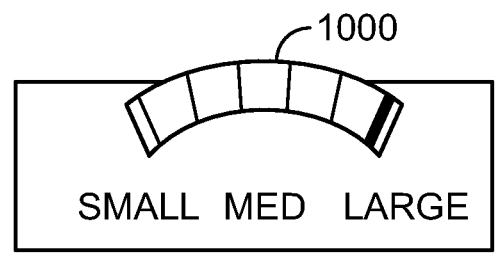
Figure 27A:
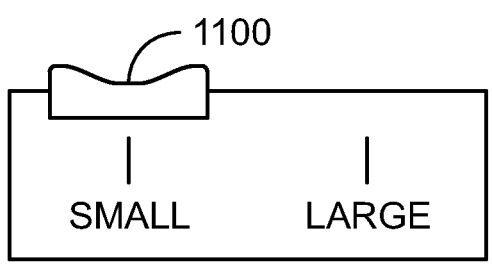
FIGS. 27A-B are enlarged views, depicting other structures that can be incorporated into the distal end portion of a tissue engagement and manipulation device.
Figure 27B:
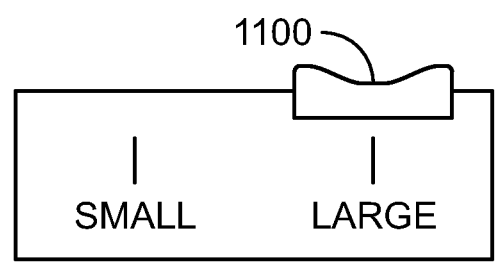

Referring now to FIG. 25A-B, expandable member 200 can be adjusted from a larger size (FIG. 25A) to a smaller size (FIG. 25B) in embodiments in which expandable member 200 includes two or more sets of arms and wings. In these embodiments, expandable member 200 can be used to capture tissue in the space between expandable member 200 and elongate tissue access assembly 104, or expandable member 200 can be used to manipulate and/or displace tissue according to other embodiments disclosed herein. The individual arms of expandable member 200 can be adjusted individually or together.

In the embodiments in which expandable member 200 can be adjusted, it is contemplated that the adjustments can occur prior to putting the device in the patient (or prior to putting the device within the sheath in the embodiments in which a sheath is used) or the adjustments can occur at or near the site of tissue manipulation within the patient. A physician can set the size of expandable member 200 based on the patient's anatomy, for example. The physician may be able to determine the desired size for expandable member 200 based on measurement and/or observation of the patient's anatomy prior to and/or during a procedure.

Referring now to FIGS. 26A-B and 27A-B, the handle of device 100 can include wheel 1000 or slider 1100, each of which are coupled to expandable member 200 and configured to expand or contract expandable member 200. In certain embodiments, wheel 1000 and slider 1100 provide continuous adjustability from a "Small" expansion size to a "Medium" expansion size to a "Large" expansion size, where the extent of expansion is indicated with a tactile indicator. Optionally, a lock is provided on wheel 1000 or slider 1100 such that the size of the expandable member can be fixed. In certain other embodiments, wheel 1000 and slider 1100 provide discrete adjustability from a "Small" expansion size to a "Medium" expansion size to a "Large" expansion size. That is, there are two or more pre-set sizes for expandable member 200 and wheel 1000 or slider 1100 allow for the physician to elect between or among those sizes only.

Various alternative methods of use are contemplated. The disclosed apparatus can be used to facilitate improving flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the disclosure has a myriad of other potential surgical, therapeutic, cosmetic or reconstructive applications, such as where a tissue, organ, graft or other material requires approximately, retracting, lifting, repositioning, compression or support.

One aspect of the invention is a system for engaging and manipulating a median lobe of a prostate gland that includes a sheath and a tissue engaging or manipulation device housed within the sheath, the tissue engaging or manipulation device being sized and shaped to be inserted within a patient's urethra and to extend within prostate tissue, the tissue engaging or manipulation device including a moveable engagement structure that can transition from a compressed state to an expanded state to enhance contact with the median lobe, wherein the engagement structure is biased to a distal end of the tissue engaging or manipulation device.

In another aspect of the invention, the engagement structure comprises a first arm and a second arm anchored to opposite sides of a shaft of the tissue engaging or manipulation device.

In another aspect of the invention, the first arm comprises a first expandable portion and the second arm comprises a second expandable portion, wherein the first expandable portion and the second expandable portion compress toward the shaft when the tissue engaging or manipulation device is housed in the sheath.

In another aspect of the invention, the first expandable portion and the second expandable portion expand away from the shaft when the tissue engaging or manipulation device exits the sheath.

In another aspect of the invention, the engagement structure further comprises a channel to receive and secure a portion of the distal end of the tissue engaging or manipulation device.

In another aspect of the invention, when the distal end of the tissue engaging or manipulation device is secured in the channel, movement of the engagement structure is constrained to a longitudinal axis of the tissue engaging or manipulation device.

In another aspect of the invention, movement along the longitudinal axis of the tissue engaging or manipulation device confers the transition of the engagement structure from the compressed state to the expanded state.

In another aspect of the invention, the engagement structure is made from a ribbon with a plurality of round edges to reduce trauma to tissue, wherein the ribbon is asymmetrical in cross-section.

In another aspect of the invention, the engagement structure is made from a ribbon with a c-shaped cross-section that reduces trauma to tissue.

In another aspect of the invention, the shaft of the tissue engaging or manipulation device further comprises a side aperture and a needle assembly that exits from the side aperture, wherein the side aperture is aligned between the first expandable portion and the second expandable portion of the engagement structure.

In another aspect of the invention, the first expandable portion includes an internal face with a first visual line marker and the second expandable portion includes an internal face and a second visual line marker.

In another aspect of the invention, the first visual line marker and the second visual line marker of the engagement structure indicate the tissue entry position for the needle assembly after exiting the side aperture.

In another aspect of the invention, the first arm and the second arm of the engagement structure are configured to be telescopic.

In another aspect of the invention, the engagement structure is a loop affixed to a terminal portion of a shaft of the tissue engaging or manipulation device.

In another aspect of the invention, the loop is flexible and configured to compress toward the shaft when the tissue engaging or manipulation device is housed in the sheath and expand when the tissue engaging or manipulation device exits the sheath.

In another aspect of the invention, the engagement structure is adjustable prior to or during a procedure, and the adjustment can be continuous or discrete via a control device on the handle of the system.

In another aspect of the invention, the engagement structure is configured to enhance frictional contact with the median lobe.

In another aspect of the invention, the engagement structure includes one or more of spikes, fangs, hooks, barbs or other protuberances arranged at various angles and having various lengths.

In another aspect of the invention, the engagement structure is defined by a knurled surface.

In another aspect of the invention, the engagement structure is defined by an adhesive surface, which optionally may be swellable.

In another aspect of the invention, the engagement structure is defined by scales.

In another aspect of the invention the system includes a first projectable needle and a second projectable needle.

In another aspect of the invention, a reinforcing structure is affixed to a terminal and of one or more of the first and second project of needles.

In another aspect of the invention, the engagement structure includes and atraumatic tape that is configured to cover the engagement structure.

In another aspect of the invention, the engagement structure is defined by a divot formed on a portion of the distal end of the system, the divot sized and shaped to substantially fit a contour both target tissue.

In another aspect of the invention, tissue is pre-treated prior to being manipulated by an engagement structure, and the pre-treatment includes one or more of electro-cauterizing, botox, or incisions.

Thus, it will be apparent from the foregoing that, while particular forms of the disclosure have been illustrated and described, various modifications can be made without parting from the spirit and scope of the disclosure.

We claim:

1. A method for treating benign prostatic hyperplasia, comprising:

inserting an introducer sheath longitudinally through a urethra of a subject until at least a distal portion of the introducer sheath is positioned within a prostatic urethra;

visualizing the prostatic urethra using a cystoscope; and advancing an elongate delivery device through the introducer sheath until at least a distal portion of the elongate delivery device extends beyond a distal opening of the introducer sheath and into a bladder, wherein the distal portion of the elongate delivery device delivers an expandable implant comprising connected curved portions that form a closed looped structure configured to engage and manipulate a prostate gland when expanded outside the introducer sheath, wherein the curved portions are biased away from a midline defined by a longitudinal axis of the elongate delivery device such that the curved portions are compressed toward the midline when positioned within the introducer sheath and expand away from the midline when positioned outside the introducer sheath.

2. The method of claim 1, further comprising turning the elongate delivery device to align the expandable implant with a lateral prostatic lobe.

3. A method for treating benign prostatic hyperplasia, comprising:

inserting an introducer sheath longitudinally through a urethra of a subject until at least a distal portion of the introducer sheath is positioned within a prostatic urethra; and advancing an elongate delivery device through the introducer sheath until at least a distal portion of the elongate delivery device extends beyond a distal opening of the introducer sheath into a bladder, wherein the distal portion of the elongate delivery device delivers an expandable implant comprising curved portions that form a closed looped structure configured to engage and manipulate a prostate gland when expanded, wherein the expandable implant is biased to an expanded configuration such that the expandable implant expands when positioned outside the introducer sheath and compresses when positioned within the introducer sheath, wherein at least a portion of the expandable implant is visualized using a cystoscope.

4. The method of claim 3, further comprising visualizing at least a portion of the elongate delivery device using the cystoscope.

5. The method of claim 3, wherein the expandable implant comprises arms and the curved portions comprise wings.

6. The method of claim 5, wherein the curved portions, arms, or wings are connected by a distal connecting member.

7. The method of claim 5, wherein the curved portions, arms, or wings connect at distal ends thereof to form the closed looped structure.

8. The method of claim 3, wherein the expandable implant expands away from a longitudinal axis of the elongate delivery device when positioned outside the introducer sheath.

* * * * *